(12) United States Patent
Maris et al.

(10) Patent No.: US 8,946,506 B2
(45) Date of Patent: Feb. 3, 2015

(54) PLANTS HAVING TOMATO TORRADO VIRUS RESISTANCE

(75) Inventors: Paulus Cornelis Maris, Benthuizen (NL); Anita Afke de Haan, Bleiswijk (NL); Johannes Hendrikus Maria Barten, Roquetas de Mar (ES); Johannes Franciscus Johanna Maria van den Heuvel, Rotterdam (NL)

(73) Assignee: Monsanto Invest B.V., Bergschenhoek (NL)

( * ) Notice: Subject to any disclaimer, the term of this patent is extended or adjusted under 35 U.S.C. 154(b) by 1063 days.

(21) Appl. No.: 12/325,310

(22) Filed: Dec. 1, 2008

(65) Prior Publication Data

US 2009/0188007 A1   Jul. 23, 2009

Related U.S. Application Data

(63) Continuation of application No. PCT/NL2007/050260, filed on Jun. 1, 2007.

(60) Provisional application No. 60/803,663, filed on Jun. 1, 2006.

(30) Foreign Application Priority Data

Jun. 1, 2006 (EP) ..................... 06076141
Apr. 25, 2007 (NL) ..................... 1033758

(51) Int. Cl.
| | | |
|---|---|---|
| *A01H 1/00* | (2006.01) | |
| *A01H 1/02* | (2006.01) | |
| *C12N 5/00* | (2006.01) | |
| *C12Q 1/68* | (2006.01) | |
| *C12Q 1/70* | (2006.01) | |
| *A01H 5/08* | (2006.01) | |
| *A01H 1/04* | (2006.01) | |
| *A01H 5/00* | (2006.01) | |

(52) U.S. Cl.
CPC .. *A01H 5/08* (2013.01); *A01H 1/04* (2013.01); *A01H 5/00* (2013.01)
USPC ........... 800/267; 800/265; 800/266; 800/279; 800/301; 800/317; 435/5; 435/6.11

(58) Field of Classification Search
USPC .............................................. 800/267; 435/5
See application file for complete search history.

(56) References Cited

U.S. PATENT DOCUMENTS 7,531,716 B2 * 5/2009 Polston et al. ................ 800/279
7,615,689 B2 * 11/2009 Hoogstraten et al. ...... 800/317.4

FOREIGN PATENT DOCUMENTS

| WO | 2006/046861 A2 | 5/2006 |
| WO | 2006/085749 A1 | 8/2006 |
| WO | 2007/139386 A1 | 12/2007 |

OTHER PUBLICATIONS

Colwyn M. Thomas, Pieter Vos, Marc Zabeau, David A. Jones, Karen A. Norcott, Brian P. Chadwick, Jonathan D.G. Jones. Identification of amplified restriction fragment polymorphism (AFLP) markers tightly linked to the tomato Cf-9 gene for resistance to *Cladosporium fulvum*. The Plant Journal (1995) 8(5), 785-794.
J.P.W. Haanstra, C. Wye, H. Verbakel, F. Meijer-Dekens, P. Van Den Berg, P. Odinot, A.W. Van Heusden, S. Tanksley, P. Lindhout, J. Peleman. An Integrated high-density RFLP-AFLP map of tomato based on two *Lycopersicon esculentum* x L. pennellii F2 populations. Theo Appl Genet (1999) 99: 254-271.
H.A. Agrama and J.W. Scott. Quantitative Trait Loci for Tomato Yellow Leaf Curl Virus and Tomato Mottle Virus Resistance in Tomato. J. Amer. Soc. Hort. Sci. 2006. 131(2): 267-272.
Luis Mejia. Evaluation of tomato germplasm for resistance to geminiviruses in Sanarate, GT. Mar. 2003. http://www.plantpath.wisc.edu/GeminivirusResistantTomatoes/CDR/Mar03/ChocSpot.htm.
Martin Verbeek, Annette M. Dullemans and Rene A.A. Van Der Vlugt. (Abstract) Tomato torrado virus, a new virus infecting tomato, presented at Advances in Plant Virology; Association of Applied Biologists c/o Warwick HRI, on Apr. 5-7, 2006.
Yulling Bai, Cai-Cheng Huang, Ron Van Der Hulst, Fien Meijer-Dekens, Guusje Bonnema, and Pim Lindhout. QTLs for Tomato Powdery Mildew Resistance (Oidium lycopersici) in Lycopersicon parviflorum G1.1601 Co-localize with Two Qualitative Powdery Mildew Resistance Genes. MPMI vol. 16, No. 2, 2003, pp. 169-176. Publication No. M-2002-1126-01R.
Weisser, M., "Development of random markers for detection of traits involved in long shelf life in lettuce and map based cloning of the tomato torrado virus resistance gene in tomato crop," Wageningen University, Plant Breeding Department, Wageningen, NL, 2010.
De Ruiter Seeds, "Tomato variety 'Torero,'" 2010.

* cited by examiner

*Primary Examiner* — Medina A Ibrahim
(74) *Attorney, Agent, or Firm* — Dentons US LLP

(57) ABSTRACT

The present invention relates to a tomato plant having within its genome at least one allele of a gene that confers resistance to Tomato torrado virus (ToTV), said virus having been deposited with the Deutsche Sammlung von Mikroorganismen und Zellkulturen GmbH on 24 Nov. 2004 under depositors reference number ToTV-E01 (DSM 16999).

17 Claims, 2 Drawing Sheets

PLANTS HAVING TOMATO TORRADO VIRUS RESISTANCE

RELATED APPLICATIONS

This application is a continuation of PCT application no. PCT/NL2007/050260, designating the United States and filed Jun. 1, 2007; which claims the benefit of the filing date of Dutch application no. NL 1033758, filed Apr. 25, 2007; which claims the benefit of the filing dates of European application no. EP 06076141.8 and U.S. provisional application No. 60/803,663, both filed Jun. 1, 2006; each of which is hereby incorporated herein by reference in its entirety for all purposes.

FIELD OF THE INVENTION

The invention relates to virus resistant plants and to methods of producing such plants. In particular, the method relates to plants that are resistant to Tomato torrado virus (ToTV), to methods of producing such plants and to plants and plant parts thus obtained.

BACKGROUND OF THE INVENTION

The tomato *Solanum lycopersicum* (formerly *Lycopersicon esculentum*) is susceptible to a large number of viral species. Some of the most prominent tomato viruses include Tomato spotted wilt virus (TSWV; genus *Tospovirus*); Pepino mosaic virus (PepMV; genus *Potexvirus*), and Tomato yellow leaf curl virus (TYLCV; genus *Begomovirus*). The damage that these diseases inflict on the plant range from discoloration of leaves and necrotic lesions, to severe crop loss and death of the plant.

The ability to provide resistant plants is of utmost importance to commercial breeders, and for some of the economically most damaging viruses, resistant plant varieties have been produced. However, from time to time, new viruses emerge that may inflict considerable damage on crops.

In 1996 a new tomato virus was reported which had infected tomato plants in the USA and Italy since 1993, and was named Tomato infectious chlorosis virus (TICV; genus *Crinivirus*; Duffus et al., 1996). Another new tomato virus of the same genus was reported in 1998. This virus was shown to have infected tomato plants in the USA since 1989 and was named Tomato chlorosis virus (ToCV; Wisler et al., 1998). Both these new viruses proved to be spread by a whitefly, the insect being a very effective disease-transmission vector.

It is generally believed that the geographic distribution of known viruses will increase and that new viruses will continue to appear, partly as a result of recombination of different viruses to form new strains or new viruses. The development of resistant cultivars can play an important role in the successful management of these diseases.

Recently, a new virus was discovered on tomato plants from Spain, which caused symptoms (locally known as the disease "torrado") that could not be attributed to any known virus. The plants exhibited necrotic lesions on leaves and brown rings on fruits and showed reduced growth. Serological tests (ELISA) indicated the presence of Pepino mosaic virus (PepMV). Electron microscopic investigations indeed revealed the rod-like particles typical for potexviruses. However, also spherically shaped viral particles were found in infected leaf tissue. The inventors were able to separate the new virus from the complex with PepMV. The new virus was tentatively named Tomato torrado virus (ToTV), was deposited with the Deutsche Sammlung von Mikroorganismen und Zellkulturen GmbH on 24 Nov. 2004 under depositors reference number ToTV-E01 (DSM 16999), and is the causative agent of diseases affecting tomato known as "torrado" (Spain), "marchitez" or "chocolate" (Mexico and Guatemala). It is believed that the virus is also capable of causing disease symptoms which are similar to those caused in tomato in other genera of *Solanum*, notably in *Capsicum* spp. (Pepper) and *Solanum melongena* (Aubergine).

At present there are no plants known that harbour specific resistance to this new virus, while there is a need for developing such resistant plants.

SUMMARY OF THE INVENTION

The present inventors have now discovered tomato plants that are resistant to ToTV. They found that, upon exposure of the plants to the virus, disease-symptoms remained absent, and that viral particles, or viral RNA could not be detected in these plants. As indicated below, this response is defined as resistant. Such plants are of pivotal importance in the development of commercially valuable varieties of cultivated tomato that are resistant to the new virus, especially when the genetic elements responsible or associated with the resistance trait, and exchanged among plants during crossing, can be followed and monitored during the breeding process. Such monitoring helps to improve the efficiency of breeding and can greatly improve the time-to-market for newly developed resistant varieties. Through crossing experiments, it was discovered that the gene responsible for the resistance to ToTV was homozygously present in the resistant plants while heterozygous plants were susceptible to ToTV infection. Thus, it was discovered that ToTV resistance is conferred by a recessive gene. Still, plants that contain both forms of the allele, i.e. heterozygous plants, are equally useful to plant breeders as they may be used as parents in crosses and selfings to produce homozygous offspring plants.

In a first aspect, therefore, the present invention relates to a tomato plant having within its genome at least one allele of a gene that confers resistance to Tomato torrado virus (ToTV), said virus having been deposited with the Deutsche Sammlung von Mikroorganismen und Zellkulturen GmbH on 24 Nov. 2004 under depositors reference number ToTV-E01 (DSM 16999). ToTV resistant tomato plants were hitherto unknown.

Upon subsequent experimentation, the inventors found that the resistance in these ToTV resistant tomato plants was closely linked to a number of AFLP markers. Without wishing to be bound by any theory, and despite the fact that the location of most of these markers on the genome is yet to be determined, it is believed that the gene(s) responsible for the trait is (are) located on chromosome 4. Therefore, in a preferred embodiment of said first aspect, the allele that comprises a gene that confers resistance to Tomato torrado virus (ToTV) is located in a genomic region linked to AFLP markers P14/M49-F-282, P11/M35-F-216, P21/M61-F-583, P25/M51-F-131, P15/M49-F-330, and/or P13/M38-F-311/313, preferably to AFLP markers P14/M49-F-282, P11/M35-F-216 and/or P13/M38-F-311/313, most preferably to AFLP markers P11/M35-F-216 and/or P13/M38-F-311/313.

In a preferred embodiment of said first aspect, said allele is located on chromosome 4, preferably in a genomic region positioned between AFLP markers P14/M49-F-282 and P11/M35-F-216.

In another preferred embodiment of said first aspect, said allele is present in homozygous form, which results in the plant expressing the resistant phenotype.

In still another preferred embodiment of said first aspect, said tomato plant is a plant of the species *Solanum lycopersicum*, preferably a cultivated tomato plant.

In yet another preferred embodiment of said first aspect, said resistance is expressed as a resistance to the establishment of an infection with ToTV upon exposure of said plant to at least the minimal infective dosage of the virus. The skilled person will understand that the minimal effective dosage can be determined by routine experimentation on susceptible plants.

In yet another preferred embodiment of said first aspect, said plant is identified in a resistance bioassay involving infection with ToTV, or wherein said plant is identified by screening for the presence of at least one molecular marker linked to said allele of said ToTV resistance gene.

In yet another preferred embodiment of said first aspect, said plant is produced by a method involving screening for the presence of at least one molecular marker linked to said allele of said ToTV resistance gene In a further aspect, the present invention relates to a plant part derived from a plant of the present invention. Examples of plant parts include, but are not limited to, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like. Preferably said part is a fruit or seed. Other preferred embodiments of plant parts include parts for vegetative propagation including such preferred parts as microspores, pollen, ovules, leaves, embryos, roots, root tips, anthers, flowers, fruits, stems shoots, stems, shoots, scions, rootstocks, protoplasts, calli, and meristemic tissue and the like.

In a further aspect, the present invention relates to a method for selecting a tomato plant that is resistant to the Tomato torrado virus (ToTV) as defined herein, said method comprising the steps of:
a) providing an inoculum of said virus;
b) exposing a tomato plant to said inoculum;
c) allowing for a sufficient incubation time, and
d) selecting said tomato plant in case no infection establishes in said plant upon lapse of said incubation time.

In a further aspect, the present invention relates to a method for selecting a tomato plant having within its genome at least one allele of a gene that confers resistance to the Tomato torrado virus (ToTV) as defined herein, said method comprising the step of screening the genomic DNA of a tomato plant for the presence of a genomic region linked to AFLP markers P14/M49-F-282, P11/M35-F-216, P21/M61-F-583, P25/M51-F-131, P15/M49-F-330, and/or P13/M38-F-311/313, preferably to AFLP markers P14/M49-F-282, P11/M35-F-216 and/or P13/M38-F-311/313, most preferably to AFLP markers P11/M35-F-216 and/or P13/M38-F-311/313.

In still a further aspect, the present invention relates to a method for the production of a tomato plant comprising selecting a plant having within its genome at least one allele (of a gene) that confers resistance to the Tomato torrado virus (ToTV) as defined herein by performing a method for selecting a tomato plant according to the present invention and crossing said selected plant with itself or another tomato plant to produce seed, and growing said seed into a tomato plant.

In still a further aspect, the present invention relates to a method for the production of a tomato plant that is resistant to the Tomato torrado virus (ToTV) as defined herein, said method comprising the step of:
a) selecting a plant having within its genome at least one allele of a gene that confers resistance to said Tomato torrado virus (ToTV) by performing a method for selecting a tomato plant according to the present invention;
b) crossing said selected plant with another tomato plant or with itself to produce seed;
c) growing said seed into tomato plants to produce offspring plants;
d) optionally repeating the crossing and growing steps of steps b) and c), and
e) selecting from amongst the offspring plants a plant wherein said allele is present in homozygous form.

In a preferred embodiment of said method, the selection in step e) is performed by screening the DNA of said offspring plant for the homozygous presence of said genomic region linked to AFLP markers P14/M49-F-282, P11/M35-F-216, P21/M61-F-583, P25/M51-F-131, P15/M49-F-330, and/or P13/M38-F-311/313, preferably to AFLP markers P14/M49-F-282, P11/M35-F-216 and/or P13/M38-F-311/313, most preferably to AFLP markers P11/M35-F-216 and/or P13/M38-F-311/313. Alternatively, the selection in step e) is performed by a resistance bioassay using said ToTV virus or any other suitable method as described herein.

In another preferred embodiment of said method, the tomato plant is a plant of the species *Solanum lycopersicum*, more preferably a cultivated tomato plant.

In still other aspects, the present invention relates to a tomato plant obtainable by a method according to the present invention and to a plant part, preferably a fruit or seed, derived from said novel and inventive tomato plant. Said plant part in an alternative preferred embodiment comprises plant parts suitable for vegetative propagation.

In still other aspects, the present invention relates to the use of the allele that confers resistance against ToTV, which allele is located in a genomic region linked to AFLP markers P14/M49-F-282, P11/M35-F-216, P21/M61-F-583, P25/M51-F-131, P15/M49-F-330, P13/M38-F-311/313 and/or COSII/CAPS marker C2_At5g25900, preferably to AFLP markers P14/M49-F-282, P11/M35-F-216 and/or P13/M38-F-311/313, most preferably to AFLP markers P11/M35-F-216 and/or P13/M38-F-311/313 and/or COSII/CAPS marker C2_At5g25900 on chromosome 4 of tomato:
to select ToTV resistant tomato plants, or
to confer resistance to ToTV in a ToTV susceptible tomato variety by increasing the frequency of the presence of the resistant allele in said variety.

In still other aspects, the present invention relates to the use of a ToTV resistant plant for enhancing the yield of and/or for preventing yield loss in said plant resulting from ToTV infection, wherein said ToTV resistant plant is characterized by the homozygous presence of the allele located in a genomic region linked to AFLP markers P14/M49-F-282, P11/M35-F-216, P21/M61-F-583, P25/M51-F-131, P15/M49-F-330, P13/M38-F-311/313 and/or COSII/CAPS marker C2_At5g25900, preferably to AFLP markers P14/M49-F-282, P11/M35-F-216 and/or P13/M38-F-311/313, most preferably to AFLP markers P11/M35-F-216 and/or P13/M38-F-311/313 and/or COSII/CAPS marker C2_At5g25900 on chromosome 4 of tomato.

In still other aspects, the present invention relates to the use of a seed of a ToTV resistant plant of the present invention, for producing a ToTV resistant plant or for preventing the occurrence of torrado disease (or a related disease such as marchitez or chocolate spot disease) in a plant or in a population of plants.

In still other aspects, the present invention relates to the use of a plant comprising at least one allele that confers resistance to ToTV, or that is homozygous for an allele that confers resistance to ToTV, wherein said allele is located in a genomic region linked to AFLP markers P14/M49-F-282, P11/M35-F-216, P21/M61-F-583, P25/M51-F-131, P15/M49-F-330, P13/M38-F-311/313 and/or COSII/CAPS marker C2_At5g25900, preferably to AFLP markers P14/M49-F-282, P11/M35-F-216 and/or P13/M38-F-311/313, most preferably to AFLP markers P11/M35-F-216 and/or P13/M38-F-311/313 and/or COSII/CAPS marker C2_At5g25900 on chromosome 4 of tomato, as a ToTV resistant tomato plant or as a parent plant in breeding programs aimed at providing other plants with the ToTV resistant phenotype that results from the homozygous presence of said allele.

In still other aspects, the present invention relates to the use of marker P11/M35-F-216, P13/M38-F-311/313 and/or C2_At5g25900 for detecting the presence of an allele that confers resistance to ToTV in a plant. Such use would generally involve nucleic acid detection methods including such steps of isolating DNA, amplifying said isolated DNA with the marker-specific primers, and checking the amplified DNA fragment for the expected length in base pairs, optionally after digesting said amplified DNA fragment, to reveal the presence of nucleotide polymorphisms associated with the resistance allele.

In preferred embodiments of the above-described use aspects of the present invention said plant is preferably a tomato plant, most preferably a plant of a commercially valuable tomato plant, such as a tomato plant comprising commercially desirable characteristics as described inter alia herein.

DESCRIPTION OF THE PREFERRED EMBODIMENTS

Figure 1:
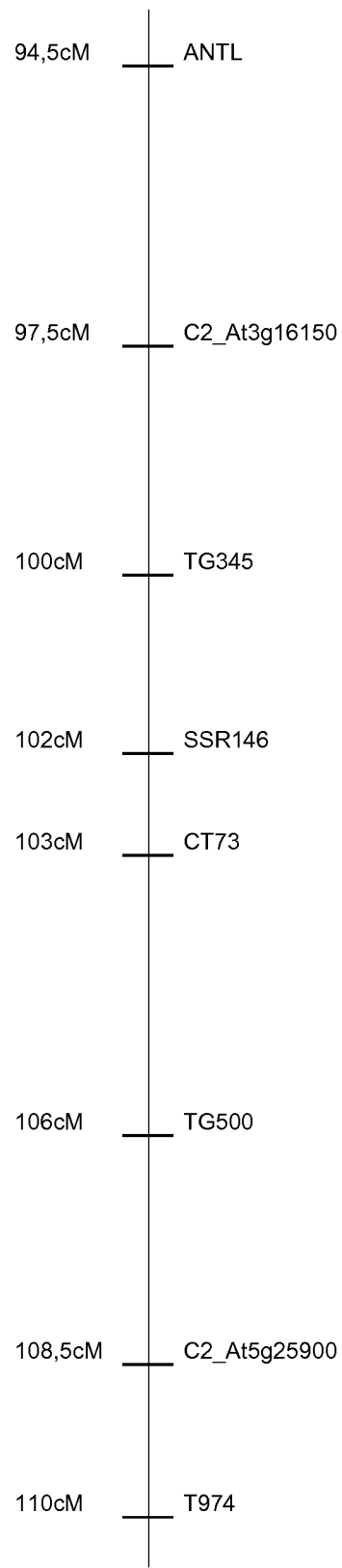
FIG. 1 show a schematic map of the tomato genome representing chromosome 4, and indicating the most recent locations of a number of well known markers.

As used herein, the term "allele(s)" means any of one or more alternative forms of a gene, all of which alleles relate to at least one trait or characteristic. In a diploid cell or organism, the two alleles of a given gene occupy corresponding loci on a pair of homologous chromosomes. Since the present invention relates to methods that comprise steps for identifying genomic regions that may comprise one or more genes, but also regulatory sequences, it is in some instances more accurate to refer to "haplotype" (i.e. an allele of a chromosomal segment) in stead of "allele", however, in those instances, the term "allele" should be understood to comprise the term "haplotype".

A "gene" is defined herein as a hereditary unit consisting of a sequence of DNA that occupies a specific location on a chromosome and that contains the genetic instruction for a particular characteristics or trait in an organism.

A "locus" is defined herein as the position that a given gene occupies on a chromosome of a given species.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

As used herein, the term "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, cleaved amplified polymorphic sequence (CAPS) markers or isozyme markers or combinations of the markers described herein which defines a specific genetic and chromosomal location.

As used herein, the term "tomato" means any plant, line or population of *Lycopersicon* including but not limited to *Lycopersicon cerasiforme*, *Lycopersicon cheesmanii*, *Lycopersicon chilense*, *Lycopersicon chmielewskii*, *Lycopersicon esculentum* (or *Solanum lycopersicum*), *Lycopersicon hirsutum*, *Lycopersicon parviflorum*, *Lycopersicon pennellii*, *Lycopersicon peruvianum*, *Lycopersicon pimpinellifolium*, or *Solanum lycopersicoides*. Wild relatives of the modern tomato have been classified within the *Lycopersicon* genus, like *L. pennellii*, *L. hirsutum*, *L. peruvianum*, *L. chilense*, *L. parviflorum*, *L. chmielewskii*, *L. cheesmanii*, *L.cerasiforme*, and *L. pimpinellifolium*. Over the past few years, there has been debate among tomato researchers and botanists whether to reclassify the names of these species. The newly proposed scientific name for the modern tomato is *Solanum lycopersicum*. Similarly, the names of the wild species may be altered. *L. pennellii* may become *Solanum pennellii*, *L. hirsutum* may become *S. habrochaites*, *L. peruvianum* may be split into *S. 'N peruvianum'* and *S. 'Callejon de Huayles*, *S. peruvianum*, and *S. corneliomuelleri*, *L. parv iflorum* may become *S.neorickii*, *L. chmielewskii* may become *S. chmielewskii*, *L. chilense* may become *S. chilense*, *L. cheesmaniae* may become *S. cheesmaniae* or *S. galapagense*, and *L. pimpinellifolium* may become *S. pimpinell ifolium* (Solanacea Genome Network (2005) Spooner and Knapp; world wide website sgn.cornell.edu/help/about/solanum_nomenclature.html).

A plant according to the present invention exists in nature. Yet it was identified as a result of a technical process. The present invention reveals two principle methods of identifying such a plant. In a first method the plant is identified by using a resistance bioassay involving exposure of a candidate plant to an effective dosage of Tomato torrado virus (ToTV) (by mechanical inoculation or exposure in the field) as defined herein. When the candidate plant remains free of disease, the symptoms of which include necrotic lesions finalizing in burn-like, full necrosis of plant material especially leafs and death of the plant and/or concentric rings of necrotic spots on fruits, said plant is said to be resistant. The plant identified by using this method comprises two alleles comprising a gene that confers resistance to Tomato torrado virus (ToTV), and is consequently homozygous for the trait.

The term "resistant to ToTV" is meant to include resistance to ToTV, including the deposited strain ToTV-E01 (DSM 16999), as well as to a related virus. A related virus in the context of the present invention is not only a virus belonging to the same taxonomic genus as ToTV, but can be defined as a virus to which resistance is conferred by the resistance allele described herein.

A plant of the present invention comprises at least one gene that confers resistance to ToTV. The locus of the gene is linked to a number of AFLP markers as herein identified. However, the location of many of these AFLP markers on the genomic map of tomato is yet unknown. Therefore, the position of the gene in the genome is not entirely certain. Since marker P14/M49-F-282 is tentatively located on chromosome 4, it is strongly suggested that the locus is located on chromosome 4. When comparing the location of publicly known markers to those of P14/M49-F-282, it appears that the gene is located in a region of which the boundaries are set by CT264 (Tomato EXPEN 2000 position 86 cM) and marker TG163 Tomato EXPEN 2000 position 135 cM). A plant of the present invention can thus be characterized in having a ToTV resistance gene located on chromosome 4 on a position between markers CT264 and TG163.

In a more detailed analysis of markers present in an experimental tomato population comprising resistant and susceptible plants, it was found that two markers were polymorphic among the population and highly correlated with the presence or absence of the resistant allele: COSII/CAPS marker C2_At5g25900 (see Example) and a bi-allelic marker referred to as P13/M38-F-311/313. These markers are positioned on Chromosome 4 of tomato and it could be calculated from the recombination frequency observed that these markers are separated by a distance of approximately 3 cM. The position of C2_At5g25900 is provided in FIG. 1. The position of P13/M38-F-311/313 relative to C2_At5g25900 could not be established due to the absence in the population tested of other polymorphic markers with known map positions. Therefore, it can thusfar be concluded that the gene that confers resistance to ToTV in tomato is associated with a region characterized by polymorphic markers C2_At5g25900 (in particular the marker producing a 420 bp and 260 bp fragment when digested with MseI, which marker is linked to the resistant allele) and P13/M38-F-311/313 (in particular P13/M38-F-313, which is linked to the resistant allele, said region covering a stretch of DNA on chromosome 4 that represents a genetic distance of approximately 3 cM, more preferably between 0 and 10 cM, still more preferably between 0 and 3.6 cM, most preferably less than 3 cM.

Figure 2:
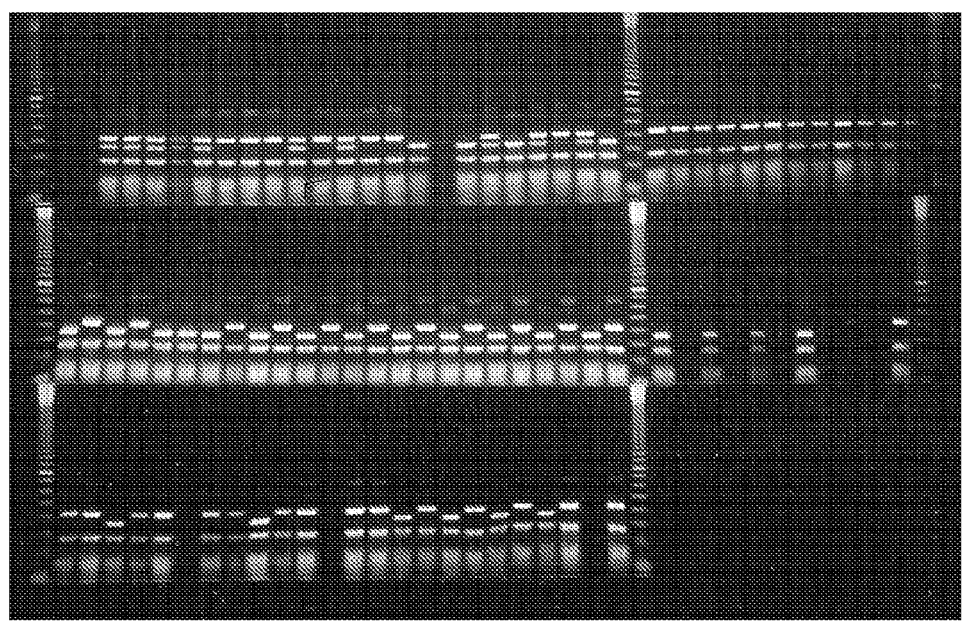
FIG. 2 shows an agarose gel with PCR fragments digested with a specific restriction enzyme to indicate the presence or absence of the resistance allele for ToTV resistance as described in Example 2.

The skilled person will be able to discern the orientation of the two markers relative to each other on the genetic map of tomato (e.g. similar to that in FIG. 2, when the distance of each to third marker can be determined. Such experiments are well within reach of the skilled person.

The plants of the present invention are found to be resistant to the viral agent that causes the tomato disease known in Mexico by the name of "marchitez". It is believed that this viral agent is the same as that deposited under accession number DSM 16999 and assigned the name Tomato torrado virus (ToTV). ToTV is the causative agent of a similar disease in tomato in Spain called "torrado". It was found that the markers as described herein that are linked to resistance to the ToTV virus deposited under accession number DSM 16999 are also linked to resistance to "marchitez". Therefore, the plants as defined herein are resistant to "torrado" as well as to "marchitez". Thus the plants as described herein confer resistance to:
  all viruses that are the causative agents of diseases which result in diseases in tomato plants with the same or similar symptoms as those caused by the deposited virus ToTV DSM 1699;
  all plant viruses that belong to the same taxon as that of ToTV (of which the taxonomic ranking still needs to be determined), preferably the plant viruses of the same family, more preferably of the same genus, still more preferably of the same species;
  ToTV DSM 16999.

In an alternative method of identifying a plant of the present invention in nature, the plant is identified by screening for the presence of at least one molecular marker linked to said at least one allele of said ToTV resistance gene. The present invention now discloses various AFLP markers which are suitable for use in such a screening assay, as they have been found to be linked to various extents to the presence of the resistance gene in tomato plants. A suitable molecular marker may be selected from the group consisting of AFLP markers P14/M49-F-282, P11/M35-F-216, P21/M61-F-583, P25/M51-F-131, P15M49-F-330, and P13/M38-F-311/313, preferably from the group consisting of AFLP markers P14/M49-F-282, P11/M35-F-216 and P13/M38-F-311/313, most preferably from the group consisting of AFLP markers P11/M35-F-216 and P13/M38-F-311/313. The Example describes the coupling between these markers and the resistance trait in more detail.

The invention further relates to a method for identifying a ToTV-resistant plant, or part thereof. There are various possibilities of identifying ToTV-resistant plants. In a first set of embodiments of such a method, active/infectious virus or full-length infectious clones may be used, whereas in an alternative embodiment only virus-detection means are used.

A first step of a method for identifying a ToTV-resistant plant using active/infectious virus comprises exposing a plant or plant part, such as a leaf or stem segment, to a infective dosage of ToTV, the aim of which is to achieve an infection. The exposure may in many cases involve the establishment of physical contact. An infective dosage may vary between plants and between ToTV-isolates tested. Theoretically, an amount of about 1 to 10 to an amount of about 500-5000 viral particles of said virus or the nucleic acids thereof will be sufficient. Infection in this way may be achieved by mechanical inoculation of purified virus particles or virus nucleic acid on healthy plants or for instance by passive inoculation via exposure to infected plants.

Alternatively, infection may be achieved by, for instance:
  growing a healthy scion on a ToTV-infected rootstock, or vice versa;
  exposing a healthy plant to transmission vectors containing the virus (including infected plants, e.g. parasitic plants like *Cuscuta* spp.);
  introducing into a healthy plant an expression vector harbouring a coding region of the ToTV virus genome;
  the use of agro-infectious clones, such as *Agrobacterium tumefaciens* strains containing an expression vector harbouring a coding region of the ToTV virus genome.

In the context of the present invention, methods for exposing a plant or plant part to an infective dosage of ToTV are not limited to any particular method.

As stated, infection may comprise mechanical inoculation of the virus on healthy plants. For instance, a portion of a diseased leaf may be rubbed directly onto a leaf of a plant that is to be infected. In an alternative procedure, an inoculum may for instance be prepared by grinding virus-containing plant tissue, preferably young leaves showing symptoms, with a mortar and pestle, or any other suitable type of homogeniser, in for instance a buffer suitable for inoculation (e.g. a 0.03 M phosphate buffer, pH 7.7). After grinding, the obtained homogenate (the sap) is preferably filtered, e.g. through cheese cloth. The sap may then be inoculation, for instance by gently contacting leaves with an amount of the sap. The leaves are preferably pre-treated in order to damage the lower epidermis and enhance entry of the virus. This may for instance be achieved by pre-dusting the leaves with carborundum powder. Excessive wounding is preferably avoided. Preferably a carborundum powder is used having microscopically small angular particles of silicon carbide (400-500 mesh). Carborundum powder may also be added directly to the sap, in which case the pre-treatment is omitted. The sap may, for instance, be applied by the forefinger, a pad of sap-soaked foam or fabric, or even with the pestle used for grinding, a glass spatula, a stiff brush, or a spray gun. After inoculation, the leaves are preferably immediately washed with water.

A second step of a method for identifying a ToTV-resistant plant comprises identifying said plant as a ToTV-resistant plant when, after said exposure, either i) disease-symptoms in said plant or plant part remain absent or are delayed in expression or are at least reduced in severity or are localized relative to a susceptible and/or sensitive control plant, and/or ii) ToTV virus or ToTV genomic sequences are not present in said plant or plant part or the presence of ToTV virus is at least quantitatively reduced in said plant relative to a susceptible control plant. As used herein the term localized means limited to the inoculated leaf.

Determining the development of ToTV-induced disease-symptoms in infected plants may be performed by quantitative methods, e.g. wherein the period required for the development of discernible (e.g. visible) disease-symptoms is noted, or by qualitative methods wherein, after a certain period has lapsed, the plant is inspected for symptom expression and the presence or severity of the symptoms is indicated.

In addition to determining the development of ToTV-induced disease-symptoms or as an alternative thereto, depending on the type of ToTV-resistance to be detected, the presence of the virus is detected in the plant or plant part. In order to detect the absence of virus in the test plants, any method may in principle be used. For instance, a method may be employed wherein a ToTV specific antibody, primer-set or probe according to the present invention is used. Alternatively, a portion of the test plant may be brought into contact with a susceptible indicator plant (e.g. *N. hesperis* '67A') to establish whether virus is present or absent in the test plant. The skilled person will understand that for such methods it is important to decontaminate the surface of the test plant, in order to distinguish between a transmission vector, a tolerant test-plant and a resistant test plant, since only the presence of virus in the plant cells needs to be established.

In performing the second step of a method for identifying a ToTV-resistant plant, the following results may be obtained. If, after successful inoculation (e.g. after the establishment of a plant-virus contact under conditions that would result in infection in a susceptible and sensitive control plant):

i) disease-symptoms remain absent; or viral particles, or viral RNA cannot be detected: the plant is resistant;

ii) disease-symptoms are delayed or reduced in severity; or systemic low titres of viral particles or viral RNA can be detected: the plant is partially resistant;

iii) disease-symptoms are severe, but remain local, limited to the inoculated leaf and do not systemically spread beyond inoculated tissue; or viral particles, or viral RNA can only be detected locally: the plant is hypersensitive;

iv) if disease-symptoms remain absent; and viral particles, or viral RNA can be detected: the plant is tolerant.

v) if the plant develops disease-symptoms and has high systemic virus titres, then the plant is susceptible and sensitive. Examples of such plants are the plants from which the virus of the present invention was isolated. These plants may serve as suitable control plants in methods of the present invention.

For the purpose of producing resistant plants, and from a viewpoint of phytosanitation, only outcome i), ii) and iii) may be considered of interest. For the purpose of obtaining plants suitable for the production of symptomless crops and products, outcome iv) may also be of particular commercial interest.

In an alternative embodiment of a method for identifying a ToTV-resistant plant only virus-detection means are used. For instance, a ToTV-resistant plant may be identified in the field by observing or identifying a symptomless plant among symptomatic plants and determining the absence of virus in said plant by performing a virus detection method. When such a method is performed it is preferred that a ToTV-selective polynucleotide or an antibody is used. Preferably, a method of identifying a ToTV-resistant plant requires the use of either the virus or virus-selective polynucleotide or antibody.

The present invention now discloses still a further method of identifying a ToTV-resistant plant, by determining the homozygous presence of markers linked to a putative ToTV resistance gene, for which markers several examples are provided.

The invention further relates to a method of producing a ToTV-resistant plant, or part thereof. Once a ToTV-resistant plant has been identified, this plant may serve as a donor plant of genetic material which is to be transferred from said donor plant to a recipient plant in order to provide said recipient plant with the genetic material. Transfer of genetic material from a donor plant to a recipient plant may occur by any suitable method known in the art. The genetic material will in most cases be genomic material. It is important however, that at least the resistance-conferring parts of the donor plant's genome are transferred. In the absence of methods for determining which parts of the donor plant's genome confer the ToTV resistance, the transfer may suitably occur by transferring complete chromosomes. Preferably, the ToTV-resistant plant serves as a male or female parent plant in a cross for producing resistant offspring plants, the offspring plant thereby receiving genomic material from the resistant donor and acting as the recipient plant. Although a susceptible parent in crosses is sensu stricto not necessarily a recipient plant, such a susceptible parent will herein also be included in the term recipient plant.

In a method for producing a ToTV-resistant plant, protoplast fusion can also be used for the transfer of resistance-conferring genomic material from a donor plant to a recipient plant, i.e. as a manner of crossing said plants. Protoplast fusion is an induced or spontaneous union, such as a somatic hybridization, between two or more protoplasts (cells of which the cell walls are removed by enzymatic treatment) to produce a single bi- or multi-nucleate cell. The fused cell that may even be obtained with plant species that cannot be interbred in nature, is tissue cultured into a hybrid plant exhibiting the desirable combination of traits. More specifically, a first protoplast can be obtained from a tomato plant or other plant line that exhibits resistance to infection by ToTV. For example, a protoplast from a ToTV-resistant tomato line may be used. A second protoplast can be obtained from a susceptible second plant line, optionally from another plant species or variety, preferably from the same plant species or variety, that comprises commercially desirable characteristics, such as, but not limited to disease resistance, insect resistance, valuable fruit characteristics, etc. The protoplasts are then fused using traditional protoplast fusion procedures, which are known in the art to produce the cross.

Alternatively, embryo rescue may be employed in the transfer of resistance-conferring genomic material from a donor plant to a recipient plant i.e. as a manner of crossing said plants. Embryo rescue can be used as a procedure to isolate embryo's from crosses wherein plants fail to produce viable seed. In this process, the fertilized ovary or immature seed of a plant is tissue cultured to create new plants (this method is described in detail in Pierik, 1999).

A method of producing a ToTV-resistant plant thus comprises in one embodiment the steps of identifying a ToTV-resistant donor plant or a plant comprising at least one allele of the resistance gene (a carrier plant) as described herein and crossing said ToTV-resistant donor plant or said carrier plant with a recipient plant. Subsequently, by further crossing and selfing, homozygous plants can be obtained that are resistant to the virus.

A method of producing a ToTV-resistant plant further comprises the step of selecting from offspring plants a resistant plant by performing a method for identifying a ToTV-resistant plant as described earlier.

Preferably, said recipient plant is a tomato plant of the species Solanum lycopersicum, more preferably an *S. lycopersicum* plant that possess commercially desirable characteristics. The recipient plant may be a ToTV-susceptible plant, a ToTV sensitive plant or a ToTV resistant plant. As explained above, the choice of the plant is determined by the fact that the resistance trait is recessive. The skilled person is aware of the various methodologies available to resolve such issues.

Also an aspect of the present invention is a ToTV-resistant plant, or a part thereof, obtainable by a method of the invention.

One method for producing a ToTV-resistant plant may comprise the transfer by introgression of a resistance-conferring nucleic acid sequence from a ToTV-resistant donor plant or a plant having the resistance gene in heterozygous form into a recipient plant by crossing said plants.

In one method, which is referred to as pedigree breeding, a donor plant that exhibits resistance to ToTV (homozygous) may be crossed with a recipient plant that preferably exhibits commercially desirable characteristics, such as, but not limited to, disease resistance, insect resistance, valuable fruit characteristics, etc. The resulting plant population (representing the $F_1$ hybrids) is then self-pollinated and allowed to set seed ($F_2$ seeds). The $F_2$ plants grown from the $F_2$ seeds are then screened for resistance to ToTV or for homozygous presence of markers linked to the resistance gene. Thus, the offspring population can be screened in a number of ways.

Production of ToTV-Resistant Tomato Plants by Transgenic Methods

According to another aspect of the present invention, a nucleic acid (preferably DNA) sequence comprising at least one of the markers linked to the ToTV resistance gene as identified herein, may be used for the production of a ToTV-resistant tomato plant. Once identified in a suitable donor tomato plant, the nucleic acid sequence that comprises a gene for ToTV-resistance, may be transferred to a suitable recipient plant by any method available. For instance, the said nucleic acid sequence may be transferred by crossing a ToTV-resistance donor tomato plant with a susceptible recipient tomato plant (i.e. by introgression), by transformation, by protoplast fusion, by a doubled haploid technique or by embryo rescue or by any other nucleic acid transfer system, optionally followed by selection of offspring plants comprising the gene heterozygous or homozygous and/or exhibiting ToTV-resistance. For transgenic methods of transfer a nucleic acid sequence comprising a gene for ToTV-resistance, may be isolated from said donor plant by using methods known in the art and the thus isolated nucleic acid sequence may be transferred to the recipient plant by transgenic methods, for instance by means of a vector, in a gamete, or in any other suitable transfer element, such as a ballistic particle coated with said nucleic acid sequence.

Plant transformation generally involves the construction of an expression vector that will function in plant cells. In the present invention, such a vector comprises a nucleic acid sequence that comprises a gene for ToTV-resistance, which vector may comprise a ToTV-resistance-conferring gene that is under control of or operatively linked to a regulatory element, such as a promoter. The expression vector may contain one or more such operably linked gene/regulatory element combinations, provided that at least one of the genes contained in the combinations encodes for ToTV-resistance. The vector(s) may be in the form of a plasmid, and can be used, alone or in combination with other plasmids, to provide transgenic plants that are resistant to ToTV, using transformation methods known in the art, such as the *Agrobacterium* transformation system.

Expression vectors can include at least one marker gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, marker-less transformation can be used to obtain plants without mentioned marker genes, the techniques for which are known in the art.

One method for introducing an expression vector into a plant is based on the natural transformation system of *Agrobacterium* (see e.g. Horsch et al., 1985). A. tumefaciens and A. rhizogenes are plant pathogenic soil bacteria that genetically transform plant cells. The Ti and Ri plasmids of *A. tumefaciens* and *A. rhizogenes*, respectively, carry genes responsible for genetic transformation of the plant (see e.g. Kado, 1991). Methods of introducing expression vectors into plant tissue include the direct infection or co-cultivation of plant cells with *Agrobacterium tumefaciens* (Horsch et al., 1985). Descriptions of *Agrobacterium* vectors systems and methods for Agrobacterium-mediated gene transfer provided by Gruber and Crosby, 1993 and Moloney et al., 1989. See also, U.S. Pat. No. 5,591,616. General descriptions of plant expression vectors and reporter genes and transformation protocols and descriptions of *Agrobacterium* vector systems and methods for *Agrobacterium*-mediated gene transfer can be found in Gruber and Crosby, 1993. General methods of culturing plant tissues are provided for example by Miki et al., 1993 and by Phillips, et al., 1988. A proper reference handbook for molecular cloning techniques and suitable expression vectors is Sambrook and Russell (2001).

Another method for introducing an expression vector into a plant is based on microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes (See, Sanford et al., 1987, 1993; Sanford, 1988, 1990; Klein et al., 1988, 1992). Another method for introducing DNA to plants is via the sonication of target cells (see Zhang et al., 1991). Alternatively, liposome or spheroplast fusion has been used to introduce expression vectors into plants (see e.g. Deshayes et al., 1985 and Christou et al., 1987). Direct uptake of DNA into protoplasts using $CaCl_2$ precipitation, polyvinyl alcohol or poly-L-ornithine has also been reported (see e.g., Hain et al. 1985 and Draper et al., 1982). Electroporation of protoplasts and whole cells and tissues has also been described (D'Halluin et al., 1992 and Laursen et al., 1994).

Following transformation of tomato target tissues, expression of the above described selectable marker genes allows for preferential selection of transformed cells, tissues and/or plants, using regeneration and selection methods now well known in the art. The markers as defined herein may also be used for that purpose.

Production of ToTV-Resistant Tomato Plants by Non-Transgenic Methods

In an alternative embodiment for producing a ToTV-resistant tomato plant, protoplast fusion can be used for the transfer of nucleic acids from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, that may even be obtained with plant species that cannot be crossed in nature, is tissue cultured into a hybrid plant exhibiting the desirable combination of traits. More specifically, a first protoplast can be obtained from a tomato plant or other plant line that exhibits resistance to infection by ToTV. For example, a protoplast from any of the resistant lines as indicated in the Example can be used. A second protoplast can be obtained from a second tomato or other plant variety, preferably a tomato line that comprises commercially desirable characteristics, such as, but not limited to disease resistance, insect resistance, valuable fruit characteristics, etc. The protoplasts are then fused using traditional protoplast fusion procedures, which are known in the art.

Alternatively, embryo rescue may be employed in the transfer of a resistance gene from a donor plant to a recipient plant. Embryo rescue can be used as a procedure to isolate embryo's from crosses wherein plants fail to produce viable seed. In this process, the fertilized ovary or immature seed of a plant is tissue cultured to create new plants (Pierik, 1999).

The present invention also relates to a method of producing a ToTV-resistant tomato plant comprising the steps of performing a method for detecting the presence of an allele associated with resistance to ToTV in a donor tomato plant according to invention as described above, and transferring a nucleic acid sequence comprising said allele thus detected, from said donor plant to a ToTV-susceptible recipient tomato plant. The transfer of said nucleic acid sequence may be performed by any of the methods previously described herein.

A preferred embodiment of such a method comprises the transfer by introgression of said nucleic acid sequence from a ToTV-resistant donor tomato plant into a ToTV-susceptible recipient tomato plant by crossing said plants. This transfer may thus suitably be accomplished by using traditional breeding techniques. The ToTV resistance genes are preferably introgressed into commercial tomato varieties by using marker-assisted breeding (MAS). Marker-assisted breeding or marker-assisted selection involves the use of one or more of the molecular markers for the identification and selection of those offspring plants that contain one or more of the genes that encode for the desired trait. In the present instance, such identification and selection is preferably based on selection of markers associated with the resistance gene as identified herein.

ToTV-Resistant Tomato Plants and Seeds

A ToTV-resistant tomato plant, or a part thereof, obtainable by a method of the invention is also an aspect of the present invention.

The ToTV-resistant tomato plants of the present invention can be of any genetic type such as inbred, hybrid, haploid, dihaploid, parthenocarp or transgenic. Further, the plants of the present invention may be heterozygous or homozygous for the resistance trait, preferably homozygous. Although the allele identified in the present invention, may be transferred to any plant in order to provide for a ToTV-resistant plant, the methods and plants of the invention are preferably related to plants of the Solanaceae family, more preferably tomato.

Inbred ToTV-resistant tomato plant lines can be developed using the techniques of recurrent selection and backcrossing, selfing and/or dihaploids or any other technique used to make parental lines. In a method of selection and backcrossing, ToTV-resistance can be introgressed into a target recipient plant (which is called the recurrent parent) by crossing the recurrent parent with a first donor plant (which is different from the recurrent parent and referred to herein as the "non-recurrent parent"). The recurrent parent is a plant that is non-resistant or has a low level of resistance to ToTV and possesses commercially desirable characteristics, such as, but not limited to disease resistance, insect resistance, valuable fruit characteristics, etc. The non-recurrent parent exhibits ToTV resistance and comprises a nucleic acid sequence that encodes for ToTV resistance. The non-recurrent parent can be any plant variety or inbred line that is cross-fertile with the recurrent parent. The progeny resulting from a cross between the recurrent parent and non-recurrent parent are backcrossed to the recurrent parent. The resulting plant population is then screened. The population can be screened in a number of different ways. For instance, the population can be screened using a resistance bioassays or field screen as described previously herein. $F_1$ hybrid plants that exhibit a ToTV-resistant phenotype comprise the requisite nucleic acid sequence encoding for ToTV resistance, and possess commercially desirable characteristics, are then selected and selfed and selected for a number of generations (up to 5, 6, 7 or 8 generations) in order to allow for the tomato plant to become increasingly inbred. This process of continued selfing and selection can be performed for two to five or more generations. The result of such breeding and selection is the production of lines that are genetically homogenous for the genes associated with ToTV resistance as well as other genes associated with traits of commercial interest. In stead of using phenotypic pathology screens of bioassays, MAS can be performed using one or more of the hereinbefore described molecular markers, hybridization probes or polynucleotides to identify those progeny that comprise a nucleic acid sequence encoding for ToTV-resistance. Alternatively, MAS can be used to confirm the results obtained from the quantitative bioassays. Once the appropriate selections are made, the process is repeated. The process of backcrossing to the recurrent parent and selecting for ToTV-resistance is repeated for approximately five or more generations. The progeny resulting from this process are heterozygous for one or more genes that encode for ToTV-resistance. The last backcross generation is then selfed in order to provide for homozygous pure breeding progeny for ToTV-resistance.

The ToTV-resistant inbred tomato lines described herein can be used in additional crossings to create ToTV-resistant hybrid plants. For example, a first ToTV-resistant inbred tomato plant of the invention can be crossed with a second inbred tomato plant possessing commercially desirable traits such as, but not limited to, disease resistance, insect resistance, desirable fruit characteristics, etc. This second inbred tomato line may or may not be ToTV-resistant, but preferably has at least one allele for ToTV resistance as linked to the markers defined herein so that at least 50% of the offspring plants express the ToTV resistant phenotype. More preferably, the second inbred tomato line is also ToTV resistant, so that the resistant phenotype is conserved despite the crossings. In this way, the a first ToTV-resistant inbred tomato plant of the invention can be used to introgress an additional heritable trait into the second inbred tomato plant line.

Another aspect of the present invention relates to a method of producing seeds that can be grown into ToTV-resistant tomato plants. In one embodiment, the method comprises the steps of providing a ToTV-resistant tomato plant of the invention, crossing said ToTV-resistant plant with another ToTV-resistant tomato plant, and collecting seeds resulting from said cross, which when planted, produce ToTV-resistant hybrid tomato plants.

In another embodiment, the method comprises the steps of providing a ToTV-resistant tomato plant of the invention, crossing said ToTV-resistant plant with a *Solanum lycopersicum* plant, collecting seeds resulting from said cross, regenerating said seeds into plants, selecting ToTV-resistant plants by any of the methods described herein, self-crossing the selected plants for a sufficient number of generations to obtain plants that are fixed for an allele that confers ToTV-resistance in the plants, backcrossing the plants thus produced with *S. lycopersicum* plants having desirable phenotypic traits for a sufficient number of generations to obtain *S. lycopersicum* plants that are ToTV-resistant and have desirable phenotypic traits, and collecting the seeds produced from the plants resulting from the last backcross, which when planted, produce tomato plants which are ToTV-resistant.

By way of example, and not of limitation, Examples of the present invention will now be given.

Deposit Information

A representative deposit of Tomato torrado virus ToTV-E01 (also referred to in the Specification and claims as "DSM 16999"), which is disclosed herein above and referenced in the claims, was made with the Deutsche Sammlung von Mikroorganismen and Zellkulturen GmBH ("DSMZ"), located at Inhoffenstrasse 7B, 38124 Braunschweig, Germany. The date of deposit was Nov. 24, 2004, and the accession number for the deposited viral isolate, ToTV-E01, is DSM 16999. All restrictions upon the deposit will be irrevocably removed upon the granting of a patent, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

A representative deposit of the tomato variety T06PF1, also designated as 11EFT 41822, which is disclosed herein above and referenced in the claims, was made with the American Type Culture Collection (ATCC), 10801 University Blvd., Manassas, VA 20110-2209. The date of deposit was Mar. 6, 2014 and the accession number for those deposited seeds of tomato variety 11 EFT 41822 is ATCC Accession No. PTA-121067. All restrictions upon the deposit will be irrevocably removed upon the granting of a patent, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.)

EXAMPLE

Example 1

Identification of Markers Linked to the ToTV Resistance Gene in Tomato

The aim of this experiment was to identify AFLP markers linked to ToTV resistance in tomato, by use of a Bulk Segregant Analysis (BSA; Michelmore, R. W., I. Paran and R. V. Kesseli, 1991. Proc. Natl. Acad. Sci. USA, 88: 9828-9832).

ToTV resistance was found to be a monogenic recessively inherited trait. The analysis was carried out on 150 plants of a F2 tomato cultivar cross of which the F3 plants were phenotyped. For determination of a reliable phenotype, phenotyping on F3 plants was repeated several times for a subset of F2 plants. Based on the results obtained by repeated phenotyping, 18 individuals were indicated as being reliable resistant and nine plants were indicated as being reliable susceptible. These plants were used for the BSA. The phenotypic information from these individuals is listed in table 1.

Marker Identification and Verification

Marker Nomenclature

Codes by which the AFLP primer combination is commonly indicated, e.g. P14/M49-F-282, wherein P and M are the common PstI and MseI primer sequences or universal primers (Vos et al., 1995; Bai et al., 2003) followed by 2 or 3 extra selective bases as indicated by a two digit extension code. Two digit extension codes are as follows: 11: AA; 13: AG; 14: AT; 15: CA; 21: GG; 25: TG; 35: ACA; 38: ACT; 49: CAG; 51: CCA; 61: CTG. 282 is the approximated size in basepairs of the resulting polymorphic fragment (given size±2 basepairs). The size is normally rounded off but may also be given in decimals. This fragment was amplified in the plants investigated. Primer and adapter sequences are described in detail by Bai et al. 2003.

Marker TG163 (Expen 2000; SOL Genomics Network; Worldwide Website: sgn.cornell.edu/index/pl) consists of a forward and reverse primer of the following sequence:

```
Forward sequence:
                                      (SEQ ID NO: 1)
TCTGGGATCATATATGGGATCTTAGAATGCTGAAGTTTCCAGTCCTTGAT
CTCCCTGGACATACTCACTGGTAATACTCTGTGGCAATAATGAAGCTGCT
TGCCATCTCTTTAATTAGTTGAGTTTTTGATATAAGATTATTGTCTGGTC
CTTCAATGTGTGTCTCACTATGCTGCCTACAACTTAATGACTGCTAACTT
TTTTTGTTAGGGTTTAGGGTTAGAAGTTTCTTTCTGGATTACCATTTCCT
TATTGAGTAAATGCAGTTGATGTTTGTTCGCAGGACATGGACTGTCAAGT
GCAATCCCGAACATGAAGACTTAATTCTGGTTCTTTCTCTTCATTTCCTT
TATCTGTTTGTCTACCCTATGTATCTGGAAAACATACTTGTGCACACTCT
CACTGAGCC Reverse sequence:
                                      (SEQ ID NO: 2)
CTTAGAAGCTTCCGCATGAAAATGAACTGCAAACGTCATACTAGATAAAA
TTAAAGAGACCTCTTGCAAAATTCTACATTCCACCTCAGCAGCGTTAACT
CCATCATGAACACATCAAGAATACAGATTTGGAGGGGGATATACTGGAGT
GATACAAACATTAATAAAAGAGATGAGTAGTGTGGCAAAGGGATAATGAG
CTCAAAAGATGGATCACGAGTTCATACTTACTTCGAGTTGTACTGATTTA
TTTTCTTGGAAGATGAGGCTTGATTGATTCTACAACCACCTGTTAGGAAA
AAAAATGCTAAATTAAAACATGAAAACACGTGGTGCCAATTCTCAACTTA
AAATAAGACAACTCTATTAGACTATTCATCATGTATTAGAAATAATAGCA
AATTGCCAAGAATACATGCACACTCATGGGAACATTTTCTATGTTATCCT
GAAATTGGCTCAGAAGTCCAACACAAGAAAAGACACAGATG
```

Biological Material

Leaf material of a total number of 300 F2 plants was available for evaluation. Of these, a total number of 150 plants were phenotyped based on the phenotype of the F3 plants derived from these F2 individuals. Genomic DNA was isolated from leaf material of these 150 phenotyped plants (Table 1) and PstI/MseI templates for AFLP fingerprinting were generated from these DNA samples. Subsequently, a test fingerprint was generated by the use of primer combination P14/M50 on all plants.

BSA and Verification on Individuals

The BSA was started by screening 96 primer combinations on one bulk containing ten (10) individuals which are resistant to ToTV and one bulk containing nine (9) individuals which are susceptible to ToTV (Table 2). This screening resulted in the identification of three (3) candidate markers (P11/M54-F-233/235 (bi-allelic), P14/M49-F-282 and P15/M49-F-330) which were subsequently verified on 32 individuals, consisting of a total of eighteen (18) available ToTV resistant individuals, nine (9) ToTV susceptible individuals and five (5) individuals of which the phenotype could not be assessed unambiguously (Table 3). Based on this screening, marker P14/M49-F-282 appeared to be the most closely linked marker to the ToTV resistance gene.

A second BSA was performed in which 96 primer combinations were screened on the R-bulk and S-bulk (now consisting of nine and eight individuals, respectively). This screening resulted in the identification of two candidate markers (P21/M61-F-583 and P25/M51-F-131) which together with one marker from the previous BSA screening (P15/M49-F-330) were verified on the 32 aforementioned individuals (Table 3). None of the additional screened markers appeared to be closer linked than the best linked marker P14/M49-F-282, identified in the first round of BSA.

Since marker P14/M49-F-282 appeared to be the most closely linked marker, it was decided to screen this marker on all 150 phenotyped individuals. The results are presented in Table 5. A total of 17 recombinants were identified (Table 4). The phenotypes were divided into three classes:
resistant (A)=Overall infection rate is less than 25%
segregating (H)=Overall infection rate is between 25% and 75%
susceptible (B)=Overall infection rate is above 75%

Based on this classification in combination with the genotypes of marker P14/M49-F-282, a total of 28 recombinants were identified, which corresponds to a distance between the marker and the ToTV resistance gene of roughly 9.5 cM. This is in accordance with the calculated size of the window (9 cM), in which the ToTV resistance gene is located between marker P14/M49-F-282 and P11/M35-F-216 (Table 3). This calculation is based on the lines used for BSA and which were believed to be phenotyped most reliable.

Since marker P14/M49-F-282, which appeared to be the most closely linked of all markers tested, was still quite a large distance from the locus, markers that were linked more closely were desired. Therefore a third BSA screening was performed, in which 72 primer combinations were screened, bringing to total number of screened primer combinations to 263. In this third screening, nine candidate markers (in six primer combinations) were identified, which were verified on eight resistant and eight susceptible individuals (Table 3). Two markers (P11/M35-F-216 and the bi-allelic marker P13/M38-F-311/313) appeared to be the most closely linked. It should be stressed that the position of marker P11/M35-216 is tentative at present, as its position is based on a single recombinant. The two markers P11/M35-F-216 and P13/M38-F-311/313 were subsequently screened on a larger set of individuals of which no phenotypic information was available, including 17 recombinants and 28 resistant and susceptible individuals (Table 5).

Marker P13/M38-F-311 is linked to the sensitive allele. The 311-basepairs fragment that is amplified between the primers has the following sequence (278 of 311 bases have been determined reliably):

(SEQ ID NO: 3)
AGCTCTTGCAAGTTGTTCATCTTCTTTCAGTTGTGATTCACTATCTGCCA

AAAATCAAAGAAAGGAATAATTAGAAAATCAAGCAAATATAGTTTTGGT

CAAGCAAATAAACAAGTATGGCTGGTTCTCAAAAATTGTCAAAGCTAAAC

-continued
TAATAAAAAGAAGCCAGATTCCTCATAGAATGAAAAGTATTTCTATAGAA

CAACGCGCAATACCATGGATGAGCTAAATACACATACATGAAAGTACTCA

GTAGCCTTGAACACATATGATGGGAAGT

Marker P13/M38-F-313 is linked to the resistant allele. The 313-basepairs fragment that is amplified between the primers has the following sequence (284 of 313 bases have been determined reliably):

(SEQ ID NO: 4)
AGCTCTTGCAAGTTGTTCATCTTCTTTCAGTTGTGATTCACTATCTGCCA

AAAATCAAAGGAAAGGAATAATTAGAAAATCAAGCAAATATAGTTTTGGT

CAAGCAAATAAACAAGTATGGCTGGTTCTCAAAAATTGTCAAAGCTAAAC

TAATAAAAAGAAGCTAGATTCCTCATAGAATGAAAAGTATTTCTATAGAA

CAACGCGCTATACCATGGATGAGCTAAACTACACATACATGAAAGTACTC

AGTAGCCTTGAACACATATGATGGGAAGTTTACT

Marker P11/M35-F-216 is linked to the resistant phenotype. The 216-basepairs fragment that is amplified between the primers has the following sequence (185 of 216 bases have been determine reliably)

(SEQ ID NO: 5)
AATGAGGGAACATTCTTTTGGGCAAAGTGGCATTTTCTGATAATCTTCTC

ACATTCAAGAATGGTATATAACTCTTTATGACTTCACAAATATCAACTGA

TCCATTTTGGACTGCAAAATTTGTGAACTTCTTTTCCTCTGCCATAATTA

GTAAATTATATTACCAAACAATAAAATTGTTTACT

Screening Two Candidate Linked Markers on Germplasm Lines

The two markers P11/M35-F-216 and P13/M38-F-311/313 were identified as being closely linked to the ToTV resistance. It should be noted that the distance between gene and marker is difficult to determine, since interpretation of the phenotypes has a large influence on the calculated distance. These markers were screened on a germplasm set of 83 individuals. Based on this screening, marker P11/M35-F-216 appears to have a predictive value of 90.4% and marker P13/M38-F-311/313 appears to have a predictive value of 96.4% (Table 6).

Positioning of ToTV Resistance on the Tomato Genome

Experimental evidence in combination with proprietary genome maps of tomato markers suggested that marker P14/M49-F-282 was located on chromosome 4. Therefore, it is expected that the genetic basis of ToTV resistance is located on chromosome 4. Two flanking markers on chromosome 4 were discovered: the bi-allelic marker P13/M38-F-311/313 and the COSII/CAPS marker C2_At5g25900 (See Example 2). When this COS II/CAPS marker is digested with MseI, the sensitive (homozygous susceptible) phenotype provides two fragments of respectively 360 bp and 260 bp, whereas the (homozygous) resistant phenotype provides two fragments of respectively 420 bp and 260 bp; plants that exhibit all three fragments have both alleles and are heterozygous (i.e. susceptible) (see FIG. 2 for a representative gel showing the digested PCR products of a test population consisting of all three types of plants; migration is bottom to top, size markers indicate 100, 200, 300 bp etc. fragments).

The unigene sequence (ID: SGN-U228314 based on the data of 30 Jun. 2004; Unigene SGN-U332034 on 5 Apr. 2007) for COSII/CAPS marker C2_At5g25900 in Lycopersicon is:

(SEQ ID NO: 6)
AAATTGGGCTGAAACTTATGGACCTATTTATTCCATCAAAACCGGCGCAA

ATACAATTGTTGTACTCAGTTCTAGTGAACTTGCAAAGGAGGCTATGGTG

ACTAGATATTCATCCATCTCAACTAGAAAGCTAACAAACGCATTGAGAAT

CCTTACTTGTGATAAGAGTATAGTCGCGATAAGTGATTACGATGAGTTTC

ACAAGACAGCGAAGCGCCACATACTGACCAGTGTTCTAGGACCAACTGCT

CAGAAACGCTTCCGTATCCACAGGGACACCTTGGTAGAAAATGTGTCAAA

GCAACTACATGATTTGGTTAGGACTGATCCTAACGAAGCAATTAATCTAA

GGAAGTCATTTCAGTCGGAACTTTTTGGTTTAGCATTGAAACAAGCTTTG

GG

Conclusion

By screening of a total of 263 PstI/MseI PCs on two bulks of resistant en susceptible individuals and subsequent verification steps, a total of four markers (one bi-allelic) appeared to be linked to ToTV resistance. The distance between the markers and the ToTV resistance gene is difficult to determine, but based on the translated phenotypes and genotypes of marker P14/M49-F-282 the distance is estimated at 9.5 cM. This is in accordance with the calculated size of the window, 9 cM in which the ToTV resistance gene is located. This calculation is based on the lines which are believed to be phenotyped most reliable.

Markers P11/M35-F-216 and P13/M38-F-311/313 (bi-allelic) were verified on 83 germplasm individuals. Based on this screening, the markers have a predictive value of 90.4% and 96.4% respectively. The occurrence of deviating lines might be explained by allelic variation at the ToTV locus or recombination.

The ToTV resistance gene is most likely located on chromosome 4 as indicated by the presence of marker P14/M49-F-282 on that chromosome.

Based on the relatively high number of candidate linked markers identified by use of 263 PCs, it is likely that the ToTV resistance gene is an introgression from a wild tomato accession.

TABLE 1

Overview of the F2 individuals and the phenotypes for ToTV resistance.

| | Experiment 1 | | | | Experiment 2 | | | | | | Overall | | |
|---|---|---|---|---|---|---|---|---|---|---|---|---|---|
| | Replication 1 | | Replication 2 | | Replication 3 | | Replication 4 | | Replication 5 | | | | |
| Plant nr | # infected pl | total # pl tested | # infected pl | total # pl tested | # infected pl | total # pl tested | # infected pl | total # pl tested | # infected pl | total # pl tested | % infected | stdev in % | in BSA |
| 1 | 7 | 9 | 7 | 9 | | | | | | | | | |
| 2 | 5 | 9 | 6 | 9 | | | | | | | | | |
| 3 | 3 | 9 | 8 | 9 | | | | | | | | | |
| 4 | 0 | 9 | 0 | 9 | 0 | 9 | 0 | 9 | 0 | 9 | 0.0 | 0.0 | R |
| 5 | 0 | 9 | 2 | 9 | | | | | | | | | |
| 8 | 8 | 9 | 9 | 9 | 5 | 9 | 8 | 9 | 4 | 6 | 81.0 | 18.3 | S |
| 10 | 6 | 9 | 5 | 9 | | | | | | | | | |
| 12 | 5 | 9 | 6 | 9 | | | | | | | | | |
| 18 | 1 | 9 | 0 | 9 | | | | | | | | | |
| 19 | 0 | 9 | 0 | 8 | 0 | 9 | 0 | 9 | 0 | 9 | 0.0 | 0.0 | R |
| 20 | 5 | 7 | 2 | 7 | | | | | | | | | |
| 21 | 9 | 9 | 9 | 9 | 7 | 9 | 7 | 9 | 6 | 9 | 84.4 | 14.9 | S |
| 22 | 5 | 8 | 6 | 9 | | | | | | | | | |
| 26 | 1 | 9 | 0 | 9 | | | | | | | | | |
| 28 | 2 | 9 | 1 | 9 | | | | | | | | | |
| 29 | 1 | 6 | 4 | 7 | | | | | | | | | |
| 30 | 3 | 9 | 5 | 9 | | | | | | | | | |
| 31 | 6 | 9 | 7 | 9 | | | | | | | | | |
| 32 | 8 | 9 | 9 | 9 | | | | | | | | | |
| 33 | 7 | 9 | 0 | 9 | | | | | | | | | |
| 34 | 2 | 9 | 0 | 9 | | | | | | | | | |
| 35 | 5 | 9 | 4 | 9 | | | | | | | | | |
| 36 | 9 | 9 | 9 | 9 | | | | | | | | | |
| 37 | 1 | 9 | 3 | 9 | | | | | | | | | |
| 39 | 5 | 8 | 9 | 9 | 4 | 9 | 4 | 9 | 7 | 9 | 65.9 | 23.6 | no |
| 40 | 0 | 8 | 0 | 9 | 0 | 9 | 0 | 9 | 0 | 9 | 0.0 | 0.0 | R |
| 45 | 8 | 9 | 9 | 9 | 6 | 9 | 8 | 9 | 5 | 9 | 80.0 | 18.3 | S |
| 46 | 0 | 9 | 0 | 9 | 0 | 9 | 0 | 9 | 0 | 9 | 0.0 | 0.0 | R |
| 47 | 8 | 9 | 7 | 9 | 4 | 9 | 4 | 9 | 8 | 9 | 68.9 | 22.8 | no |
| 49 | 0 | 9 | 0 | 9 | 0 | 9 | 0 | 9 | 0 | 9 | 0.0 | 0.0 | R |
| 50 | 3 | 9 | 3 | 9 | | | | | | | | | |
| 52 | 0 | 9 | 0 | 9 | 0 | 9 | 0 | 9 | 0 | 9 | 0.0 | 0.0 | R |
| 53 | 8 | 9 | 8 | 9 | 6 | 9 | 9 | 9 | 6 | 9 | 82.2 | 14.9 | S |
| 54 | 2 | 9 | 0 | 9 | | | | | | | | | |
| 57 | 2 | 9 | 2 | 9 | | | | | | | | | |
| 58 | 5 | 9 | 8 | 9 | | | | | | | | | |
| 59 | 6 | 9 | 6 | 9 | | | | | | | | | |
| 63 | 8 | 9 | 6 | 9 | | | | | | | | | |
| 64 | 3 | 9 | 5 | 9 | | | | | | | | | |
| 65 | 5 | 9 | 8 | 9 | | | | | | | | | |
| 68 | 1 | 9 | 0 | 8 | | | | | | | | | |

TABLE 1-continued

Overview of the F2 individuals and the phenotypes for ToTV resistance.

| | Experiment 1 | | | | Experiment 2 | | | | | | Overall | | |
|---|---|---|---|---|---|---|---|---|---|---|---|---|---|
| | Replication 1 | | Replication 2 | | Replication 3 | | Replication 4 | | Replication 5 | | | | |
| Plant nr | # infected pl | total # pl tested | # infected pl | total # pl tested | # infected pl | total # pl tested | # infected pl | total # pl tested | # infected pl | total # pl tested | % infected | stdev in % | in BSA |
| 69 | 1 | 9 | 0 | 9 | | | | | | | | | |
| 70 | 0 | 9 | 0 | 9 | 0 | 9 | 0 | 9 | 0 | 9 | 0.0 | 0.0 | R |
| 71 | 0 | 9 | 0 | 9 | | | | | | | | | |
| 75 | 1 | 9 | 0 | 9 | | | | | | | | | |
| 76 | 6 | 9 | 6 | 8 | | | | | | | | | |
| 78 | 8 | 9 | 8 | 9 | 8 | 9 | 6 | 8 | 5 | 9 | 79.5 | 14.6 | S |
| 79 | 8 | 9 | 8 | 9 | 6 | 9 | 4 | 9 | 5 | 9 | 68.9 | 19.9 | no |
| 81 | 6 | 9 | 5 | 9 | | | | | | | | | |
| 82 | 0 | 9 | 0 | 9 | 0 | 9 | 0 | 9 | 0 | 9 | 0.0 | 0.0 | R |
| 83 | 9 | 9 | 8 | 9 | 7 | 9 | 7 | 9 | 4 | 9 | 77.8 | 20.8 | S |
| 84 | 0 | 8 | 0 | 9 | 0 | 9 | 1 | 9 | 0 | 9 | 2.3 | 5.0 | no |
| 85 | 0 | 9 | 0 | 8 | | | | | | | | | |
| 87 | 0 | 9 | 4 | 9 | | | | | | | | | |
| 89 | 7 | 9 | 7 | 9 | 7 | 9 | 4 | 9 | 5 | 9 | 66.7 | 15.7 | no |
| 90 | 0 | 8 | 1 | 9 | | | | | | | | | |
| 92 | 5 | 9 | 7 | 9 | | | | | | | | | |
| 94 | 7 | 9 | 6 | 9 | | | | | | | | | |
| 95 | 0 | 9 | 0 | 9 | 0 | 9 | 0 | 9 | 0 | 9 | 0.0 | 0.0 | R |
| 96 | 0 | 8 | 0 | 9 | | | | | | | | | |
| 102 | 0 | 9 | 0 | 9 | | | | | | | | | |
| 105 | 6 | 9 | 5 | 9 | | | | | | | | | |
| 108 | 1 | 9 | 0 | 9 | | | | | | | | | |
| 112 | 0 | 9 | 0 | 9 | | | | | | | | | |
| 115 | 3 | 9 | 9 | 9 | | | | | | | | | |
| 119 | 7 | 9 | 9 | 9 | 7 | 9 | 2 | 9 | 3 | 5 | 68.3 | 29 | no |
| 120 | 0 | 9 | 0 | 9 | 0 | 9 | 0 | 9 | 0 | 9 | 0.0 | 0 | R |
| 121 | 0 | 9 | 0 | 9 | | | | | | | | | |
| 122 | 3 | 9 | 7 | 9 | | | | | | | | | |
| 123 | 0 | 9 | 0 | 9 | | | | | | | | | |
| 125 | 0 | 9 | 1 | 9 | | | | | | | | | |
| 126 | 8 | 9 | 6 | 9 | 7 | 9 | 4 | 8 | 3 | 9 | 63.6 | 22.1 | no |
| 128 | 8 | 9 | 6 | 9 | 9 | 9 | 3 | 9 | 5 | 9 | 68.9 | 26.5 | no |
| 129 | 5 | 9 | 3 | 9 | | | | | | | | | |
| 130 | 0 | 9 | 0 | 9 | | | | | | | | | |
| 131 | 5 | 9 | 7 | 9 | | | | | | | | | |
| 132 | 0 | 9 | 1 | 9 | | | | | | | | | |
| 133 | 0 | 4 | 0 | 8 | 0 | 9 | 0 | 9 | 0 | 9 | 0.0 | 0 | R |
| 134 | 1 | 9 | 0 | 9 | | | | | | | | | |
| 135 | 9 | 9 | 8 | 9 | 7 | 9 | 9 | 9 | 6 | 9 | 86.7 | 14.5 | S |
| 136 | 0 | 9 | 0 | 9 | 0 | 9 | 0 | 9 | 0 | 9 | 0.0 | 0 | R |
| 137 | 0 | 9 | 1 | 9 | | | | | | | | | |
| 138 | 0 | 9 | 1 | 9 | | | | | | | | | |
| 139 | 6 | 9 | 7 | 9 | | | | | | | | | |
| 140 | 2 | 9 | 5 | 9 | | | | | | | | | |
| 142 | 8 | 9 | 6 | 9 | | | | | | | | | |
| 143 | 3 | 9 | 6 | 9 | | | | | | | | | |
| 145 | 0 | 9 | 3 | 9 | | | | | | | | | |
| 146 | 4 | 9 | 4 | 9 | | | | | | | | | |
| 147 | 8 | 9 | 3 | 9 | | | | | | | | | |
| 149 | 0 | 9 | 0 | 9 | | | | | | | | | |
| 150 | 3 | 9 | 2 | 9 | | | | | | | | | |
| 152 | 5 | 9 | 5 | 9 | | | | | | | | | |
| 153 | 3 | 9 | 3 | 9 | | | | | | | | | |
| 154 | 3 | 9 | 6 | 9 | | | | | | | | | |
| 155 | 3 | 9 | 2 | 9 | | | | | | | | | |
| 157 | 6 | 9 | 7 | 9 | | | | | | | | | |
| 160 | 0 | 9 | 2 | 9 | | | | | | | | | |
| 161 | 0 | 9 | 1 | 9 | | | | | | | | | |
| 163 | 1 | 9 | 0 | 9 | | | | | | | | | |
| 164 | 4 | 7 | 5 | 9 | | | | | | | | | |
| 165 | 0 | 9 | 1 | 9 | | | | | | | | | |
| 166 | 3 | 9 | 4 | 9 | | | | | | | | | |
| 170 | 3 | 9 | 4 | 9 | | | | | | | | | |
| 171 | 0 | 9 | 0 | 9 | 0 | 9 | 0 | 9 | 0 | 9 | 0.0 | 0.0 | R |
| 172 | 8 | 9 | 5 | 8 | 9 | 9 | 8 | 9 | 7 | 9 | 84.1 | 14.2 | S |
| 173 | 8 | 9 | 6 | 9 | | | | | | | | | |
| 174 | 4 | 9 | 4 | 9 | | | | | | | | | |
| 176 | 2 | 9 | 5 | 9 | | | | | | | | | |

TABLE 1-continued

Overview of the F2 individuals and the phenotypes for ToTV resistance.

| | Experiment 1 | | | | Experiment 2 | | | | | | Overall | | |
|---|---|---|---|---|---|---|---|---|---|---|---|---|---|
| | Replication 1 | | Replication 2 | | Replication 3 | | Replication 4 | | Replication 5 | | | | |
| Plant nr | # infected pl | total # pl tested | # infected pl | total # pl tested | # infected pl | total # pl tested | # infected pl | total # pl tested | # infected pl | total # pl tested | % infected | stdev in % | in BSA |
| 177 | 5 | 9 | 4 | 9 | | | | | | | | | |
| 178 | 7 | 9 | 8 | 9 | 9 | 9 | 7 | 9 | 6 | 9 | 82.2 | 12.7 | S |
| 179 | 0 | 8 | 0 | 9 | 0 | 9 | 0 | 9 | 0 | 9 | 0.0 | 0.0 | R |
| 180 | 1 | 9 | 2 | 9 | | | | | | | | | |
| 181 | 6 | 9 | 4 | 9 | | | | | | | | | |
| 182 | 8 | 9 | 7 | 9 | 6 | 9 | 7 | 9 | 7 | 9 | 77.8 | 7.9 | no |
| 183 | 2 | 9 | 6 | 9 | | | | | | | | | |
| 185 | 1 | 8 | 3 | 9 | | | | | | | | | |
| 186 | 0 | 9 | 0 | 9 | 0 | 9 | 0 | 9 | 0 | 9 | 0.0 | 0.0 | R |
| 189 | 6 | 9 | 7 | 9 | | | | | | | | | |
| 190 | 0 | 9 | 0 | 9 | 0 | 9 | 0 | 9 | 0 | 9 | 0.0 | 0.0 | R |
| 191 | 4 | 9 | 5 | 9 | | | | | | | | | |
| 192 | 8 | 9 | 8 | 9 | 5 | 9 | 5 | 9 | 5 | 9 | 68.9 | 18.3 | no |
| 194 | 6 | 9 | 6 | 9 | | | | | | | | | |
| 197 | 0 | 9 | 1 | 9 | | | | | | | | | |
| 198 | 6 | 9 | 7 | 9 | | | | | | | | | |
| 200 | 6 | 9 | 5 | 9 | | | | | | | | | |
| 201 | 5 | 9 | 3 | 9 | | | | | | | | | |
| 203 | 7 | 9 | 5 | 9 | | | | | | | | | |
| 205 | 5 | 9 | 4 | 9 | | | | | | | | | |
| 206 | 0 | 9 | 0 | 9 | 0 | 9 | 0 | 9 | 0 | 9 | 0.0 | 0.0 | R |
| 207 | 0 | 9 | 0 | 9 | | | | | | | | | |
| 209 | 7 | 9 | 3 | 9 | | | | | | | | | |
| 211 | 4 | 9 | 4 | 9 | | | | | | | | | |
| 212 | 0 | 9 | 0 | 9 | 0 | 9 | 1 | 5 | 0 | 8 | 2.5 | 8.9 | no |
| 212 | 6 | 9 | 6 | 9 | | | | | | | | | |
| 215 | 3 | 7 | 1 | 8 | | | | | | | | | |
| 217 | 0 | 9 | 0 | 9 | | | | | | | | | |
| 219 | 8 | 9 | 4 | 9 | | | | | | | | | |
| 221 | 6 | 9 | 5 | 9 | | | | | | | | | |
| 222 | 9 | 9 | 4 | 9 | 9 | 9 | 5 | 9 | 7 | 9 | 75.6 | 25.3 | no |
| 226 | 1 | 9 | 2 | 9 | | | | | | | | | |
| 227 | 7 | 9 | 3 | 9 | | | | | | | | | |
| 259 | 5 | 9 | 7 | 9 | | | | | | | | | |
| 262 | 0 | 9 | 0 | 9 | 0 | 9 | 0 | 9 | 0 | 9 | 0.0 | 0.0 | R |
| 275 | 5 | 9 | 6 | 9 | | | | | | | | | |
| 276 | 4 | 9 | 7 | 9 | | | | | | | | | |
| 283 | 0 | 9 | 0 | 9 | | | | | | | | | |
| 284 | 6 | 9 | 4 | 9 | | | | | | | | | |
| 300 | 0 | 5 | 2 | 9 | | | | | | | | | |
| | | | | | | | | | | | | | 18 Resistant lines |
| | | | | | | | | | | | | | 9 Susceptible lines |
| Susceptible control line (=F1 from which the F3 was derived): | | | | | | | | | | | | | |
| 62 | 12 | 14 | 7 | 7 | 7 | 7 | 7 | 9 | 7 | 7 | 85.8 | 14.9 | |
| 62 | 12 | 14 | 8 | 14 | 7 | 7 | 8 | 9 | 6 | 9 | | | |
| 62 | 7 | 9 | 34 | 35 | 8 | 9 | 8 | 9 | 9 | 9 | | | |
| 62 | 5 | 9 | 8 | 9 | 9 | 9 | 6 | 9 | | | | | |

Note,
phenotypes are based on the F3 plants derived from these F2 individuals.

TABLE 2

Used F2 individuals in the bulks used for the BSA

| Resistant pool | Susceptible pool |
|---|---|
| 004 | 008 |
| 019 | 032 |
| 040 | 045 |
| 046 | 053 |
| 049 | 078 |
| 070 | 083 |
| 082 | 135 |
| 095 | 172 |
| 136 | 178* |
| 149* | |

*Individuals only used in the first BSA

TABLE 3

Overview of the markers identified by use of BSA and which are subsequently screened on 32 F2 plants.

| Individual | Overall % infected | stdev in % | Translated phenotype KG | P11/M35-F-216<N> CIS | Phenotype DRS | P13/M38-F-311<N> TRANS | P13/M38-F-313<N> CIS | P14/M49-F-282<N> CIS | P15/M49-F-330.08<N>-P1 TRANS |
|---|---|---|---|---|---|---|---|---|---|
| T084 | 2.3 | 5.0 | B | B | ? | B | B | B | B |
| T182 | 77.8 | 7.9 | A | A | ? | A | A | A | A |
| T192 | 68.9 | 18.3 | H | H | ? | H | H | H | H |
| T212 | 2.5 | 8.9 | B | B | ? | B | B | B | C |
| T004 | 0.0 | 0.0 | B | B | R | B | B | B | B |
| T019 | 0.0 | 0.0 | B | B | R | B | B | B | B |
| T040 | 0.0 | 0.0 | B | B | R | B | B | B | B |
| T046 | 0.0 | 0.0 | B | B | R | B | B | B | B |
| T049 | 0.0 | 0.0 | B | B | R | B | B | B | B |
| T052 | 0.0 | 0.0 | B | B | R | B | B | B | B |
| T070 | 0.0 | 0.0 | B | B | R | B | B | B | B |
| T082 | 0.0 | 0.0 | B | B | R | B | B | B | B |
| T095 | 0.0 | 0.0 | B | B | R | B | B | B | B |
| T120 | 0.0 | 0.0 | B | B | R | B | B | B | B |
| T133 | 0.0 | 0.0 | B | B | R | B | B | B | B |
| T136 | 0.0 | 0.0 | B | B | R | B | B | B | B |
| T149 |  |  |  | B | R | B | B | B | B |
| T171 | 0.0 | 0.0 | B | B | R | B | B | B | C |
| T179 | 0.0 | 0.0 | B | H | R | B | B | B | B |
| T186 | 0.0 | 0.0 | B | B | R | B | B | B | H |
| T190 | 0.0 | 0.0 | B | B | R | B | B | C | H |
| T206 | 0.0 | 0.0 | B | B | R | C | B | C | H |
| T262 | 0.0 | 0.0 | B | B | R | B | B | B | H |
| T008 | 81.0 | 18.3 | A | A | S | A | A | A | A |
| T021 | 84.4 | 14.9 | A | A | S | A | A | A | A |
| T045 | 80.0 | 18.3 | A | A | S | A | A | A | A |
| T053 | 82.2 | 14.9 | A | A | S | A | A | A | A |
| T078 | 79.5 | 14.6 | A | A | S | A | A | A | A |
| T083 | 77.8 | 20.8 | A | A | S | A | A | A | A |
| T135 | 86.7 | 14.5 | A | A | S | A | A | A | A |
| T172 | 84.1 | 14.2 | A | A | S | A | A | A | A |
| T178 | 82.2 | 12.7 | A | A | S | A | A | A | A |

Markers are ordered on the most expected order. It is questioned whether marker P11/M35-F-216 is positioned correctly.

Legend
A = homozygous P1 (=susceptible)
B = homozygous P2 (=resistant)
H = Heterozygous score
D = Between A and H
C = Between B and H
U = Unknown score
R = Individual resistant
S = Individual susceptible
Translated phenotype KG:
A = Overall % infected > 75
B = Overall % infected < 25
H = 25 < 0verall % infected < 75

TABLE 4

Recombinants selected by De Ruiter Seeds on the basis of marker P14/M49-F-282<N>.

| | Individual | Overall % infected | stdev in % | Translated phenotype KG | P14/M49-F-282<N> CIS |
|---|---|---|---|---|---|
| Rec | T026 | 5.6 | | B | B |
| Rec | T037 | 22.2 | | A | B |
| Rec | T054 | 11.1 | | B | B |
| Rec | T075 | 5.6 | | B | B |
| Rec | T084 | 2.3 | 5.0 | B | B |
| Rec | T087 | 22.2 | | A | B |
| Rec | T090 | 5.9 | | B | B |
| Rec | T125 | 5.6 | | B | B |
| Rec | T132 | 5.6 | | B | B |
| Rec | T134 | 5.6 | | B | B |
| Rec | T137 | 5.6 | | B | B |
| Rec | T138 | 5.6 | | B | B |
| Rec | T145 | 16.7 | | B | B |
| Rec | T153 | 33.3 | | H | B |
| Rec | T177 | 50.0 | | H | B |

TABLE 4-continued

Recombinants selected by De Ruiter Seeds on the basis of marker P14/M49-F-282<N>.

|  | Individual | Overall % infected | stdev in % | Translated phenotype KG | P14/M49-F-282<N> CIS |
|---|---|---|---|---|---|
| Rec | T211 | 44.4 |  | H | B |
| Rec | T212 | 2.5 | 8.9 | B | B |

Legend:
A = homozygous P1 (=susceptible)
B = homozygous P2 (=resistant)
H = Heterozygous score
D = Between A and H
C = Between B and H
U = Unknown score
R = Individual resistant
S = Individual susceptible
Translated phenotype KG:
A = Overall % infected > 75
B = Overall % infected < 25
H = 25 < Overall % infected < 75
Note:
Rec are identified by De Ruiter Seeds

TABLE 5

Data generated by use of the three best linked markers. Marker P14/M49-F-282 is screened on 150 phenotype lines and the markers P11/M35-F-216 and the bi-allelic P13/M38-F-311/313 were screened on a subset.

|  | Individual | Overall % infected | stdev in % | Translated phenotype KG | P11/M35-F-216<N> CIS | Phenotype DRS | P13/M38-F-311<N> TRANS | P13/M38-F-313<N> CIS | P13/M49-F-282<N> CIS |
|---|---|---|---|---|---|---|---|---|---|
|  | T001 | 77.8 |  | A | A | S | A | A | A |
|  | T002 | 61.1 |  | H | U |  | U | U | A |
|  | T003 | 61.1 |  | H | U |  | U | U | A |
|  | T004 | 0.0 | 0.0 | B | B | R | B | B | B |
|  | T005 | 11.1 |  | B | U |  | U | U | H |
|  | T008 | 81.0 | 18.3 | A | A | S | A | A | A |
|  | T010 | 61.1 |  | H | U |  | U | U | H |
|  | T012 | 61.1 |  | H | U |  | U | U | H |
|  | T018 | 5.6 |  | B | U |  | U | U | H |
|  | T019 | 0.0 | 0.0 | B | B | R | B | B | B |
|  | T020 | 50.0 |  | H | U |  | U | U | H |
|  | T021 | 84.4 | 14.9 | A | A | S | A | A | A |
|  | T022 | 64.7 |  | H | U |  | U | U | H |
| Rec | T026 | 5.6 |  | B | B |  | B | B | B |
|  | T028 | 16.7 |  | B | U |  | U | U | B |
|  | T029 | 38.5 |  | H | U |  | U | U | H |
|  | T030 | 44.4 |  | H | U |  | U | U | H |
|  | T031 | 72.2 |  | H | U |  | U | U | H |
|  | T032 | 94.4 |  | A | A | S | A | A | A |
|  | T033 | 38.9 |  | H | B |  | B | B | B |
|  | T035 | 50.0 |  | H | U |  | U | U | H |
|  | T036 | 100.0 |  | A | A | S | A | A | A |
| Rec | T037 | 22.2 |  | A | B |  | B | B | B |
|  | T039 | 65.9 | 23.6 | H | A | S | A | A | A |
|  | T040 | 0.0 | 0.0 | B | B | R | B | B | B |
|  | T045 | 80.0 | 18.3 | A | A | S | A | A | A |
|  | T046 | 0.0 | 0.0 | B | B | R | B | B | B |
|  | T047 | 68.9 | 22.8 | H | U |  | U | U | H |
|  | T049 | 0.0 | 0.0 | B | B | R | B | B | B |
|  | T050 | 33.3 |  | H | U |  | U | U | H |
|  | T052 | 0.0 | 0.0 | B | B | R | B | B | B |
|  | T053 | 82.2 | 14.9 | A | A | S | A | A | A |
| Rec | T054 | 11.1 |  | B | B |  | B | B | B |
|  | T057 | 22.2 |  | A | U |  | U | U | H |
|  | T058 | 72.2 |  | H | U |  | U | U | H |
|  | T059 | 66.7 |  | H | U |  | U | U | H |
|  | T062 | 85.8 | 14.9 | A | U |  | U | U | H |
|  | T063 | 77.8 |  | A | U |  | U | U | H |
|  | T064 | 44.4 |  | H | U |  | U | U | H |
|  | T065 | 72.2 |  | H | U |  | U | U | A |
|  | T068 | 5.9 |  | B | U |  | U | U | B |

TABLE 5-continued

Data generated by use of the three best linked markers. Marker P14/M49-F-282 is screened on 150 phenotype lines and the markers P11/M35-F-216 and the bi-allelic P13/M38-F-311/313 were screened on a subset.

|  | Individual | Overall % infected | stdev in % | Translated phenotype KG | P11/M35-F-216<N> CIS | Phenotype DRS | P13/M38-F-311<N> TRANS | P13/M38-F-313<N> CIS | P13/M49-F-282<N> CIS |
|---|---|---|---|---|---|---|---|---|---|
|  | T069 | 5.6 |  | B | U |  | U | U | B |
|  | T070 | 0.0 | 0.0 | B | B | R | B | B | B |
|  | T071 | 0.0 |  | B | B | R | B | B | B |
| Rec | T075 | 5.6 |  | B | B |  | B | B | B |
|  | T076 | 70.6 |  | H | U |  | U | U | H |
|  | T078 | 79.5 | 14.6 | A | A | S | A | A | A |
|  | T079 | 68.9 | 19.9 | H | A | S | A | A | A |
|  | T081 | 61.1 |  | H | U |  | U | U | H |
|  | T082 | 0.0 | 0.0 | B | B | R | B | B | B |
|  | T083 | 77.8 | 20.8 | A | A | S | A | A | A |
| Rec | T084 | 2.3 | 5.0 | B | B | ? | B | B | B |
|  | T085 | 0.0 |  | B | B | R | B | B | B |
| Rec | T087 | 22.2 |  | A | B |  | B | B | B |
|  | T089 | 66.7 | 15.7 | H | U |  | U | U | H |
| Rec | T090 | 5.9 |  | B | B |  | B | B | B |
|  | T092 | 66.7 |  | H | U |  | U | U | A |
|  | T094 | 72.2 |  | H | U |  | U | U | H |
|  | T095 | 0.0 | 0.0 | B | B | R | B | B | B |
|  | T096 | 0.0 |  | B | B | R | B | B | B |
|  | T102 | 0.0 |  | B | B | R | B | B | B |
|  | T105 | 61.1 |  | H | U |  | U | U | H |
|  | T108 | 5.6 |  | B | U |  | U | U | B |
|  | T112 | 0.0 |  | B | B | R | B | B | B |
|  | T115 | 66.7 |  | H | U |  | U | U | H |
|  | T119 | 68.3 | 29.0 | H | U |  | U | U | A |
|  | T120 | 0.0 | 0.0 | B | B | R | B | B | B |
|  | T121 | 0.0 |  | B | B | R | B | B | B |
|  | T122 | 55.6 |  | H | U |  | U | U | H |
|  | T123 | 0.0 |  | B | B | R | B | B | B |
| Rec | T125 | 5.6 |  | B | B |  | B | B | B |
|  | T126 | 63.6 | 22.1 | H | U |  | U | U | H |
|  | T128 | 68.9 | 26.5 | H | U |  | U | U | H |
|  | T129 | 44.4 |  | H | U |  | U | U | H |
|  | T130 | 0.0 |  | B | B | R | B | B | B |
|  | T131 | 66.7 |  | H | U |  | U | U | A |
| Rec | T132 | 5.6 |  | B | B |  | B | B | B |
|  | T133 | 0.0 | 0.0 | B | B | R | B | B | B |
| Rec | T134 | 5.6 |  | B | B |  | B | B | B |
|  | T135 | 86.7 | 14.5 | A | A | S | A | A | A |
|  | T136 | 0.0 | 0.0 | B | B | R | B | B | B |
| Rec | T137 | 5.6 |  | B | B |  | B | B | B |
| Rec | T138 | 5.6 |  | B | B |  | B | B | B |
|  | T139 | 72.2 |  | H | U |  | U | U | H |
|  | T140 | 38.9 |  | H | U |  | U | U | H |
|  | T142 | 77.8 |  | A | U |  | U | U | A |
|  | T143 | 50.0 |  | H | U |  | U | U | H |
| Rec | T145 | 16.7 |  | B | B |  | B | B | B |
|  | T146 | 44.4 |  | H | U |  | U | U | H |
|  | T147 | 61.1 |  | H | U |  | U | U | A |
|  | T149 | 0.0 |  | B | B | R | B | B | B |
|  | T150 | 27.8 |  | H | U |  | U | U | H |
|  | T152 | 55.6 |  | H | U |  | U | U | H |
| Rec | T153 | 33.3 |  | H | B |  | H | H | B |
|  | T154 | 50.0 |  | H | U |  | U | U | H |
|  | T155 | 27.8 |  | H | U |  | U | U | H |
|  | T157 | 72.2 |  | H | U |  | U | U | A |
|  | T160 | 11.1 |  | B | U |  | U | U | B |
|  | T161 | 5.6 |  | B | U |  | U | U | B |
|  | T163 | 5.6 |  | B | U |  | U | U | B |
|  | T164 | 56.3 |  | H | U |  | U | U | H |
|  | T165 | 5.6 |  | B | U |  | U | U | B |
|  | T166 | 38.9 |  | H | U |  | U | U | H |
|  | T170 | 38.9 |  | H | U |  | U | U | H |
|  | T171 | 0.0 |  | B | B | R | B | B | B |
|  | T172 | 84.1 | 14.2 | A | A | S | A | A | A |
|  | T173 | 77.8 |  | A | U |  | U | U | H |
|  | T174 | 44.4 |  | H | U |  | U | U | H |
|  | T176 | 38.9 |  | H | U |  | U | U | H |
| Rec | T177 | 50.0 |  | H | B |  | H | H | B |
|  | T178 | 82.2 | 12.7 | A | A | S | A | A | A |
|  | T179 | 0.0 | 0.0 | B | H | R | B | B | B |
|  | T180 | 16.7 |  | B |  |  |  |  |  |
|  | T181 | 55.6 |  | H | U |  | U | U | A |

TABLE 5-continued

Data generated by use of the three best linked markers. Marker P14/M49-F-282 is screened on 150 phenotype lines and the markers P11/M35-F-216 and the bi-allelic P13/M38-F-311/313 were screened on a subset.

|  | Individual | Overall % infected | stdev in % | Translated phenotype KG | P11/M35-F-216<N> CIS | Phenotype DRS | P13/M38-F-311<N> TRANS | P13/M38-F-313<N> CIS | P13/M49-F-282<N> CIS |
|---|---|---|---|---|---|---|---|---|---|
|  | T182 | 77.8 | 7.9 | A | A | ? | A | A | A |
|  | T183 | 44.4 |  | H | U |  | U | U | H |
|  | T185 | 23.5 |  | A | U |  | U | U | H |
|  | T186 | 0.0 | 0.0 | B | B | R | B | B | B |
|  | T189 | 72.2 |  | H | B |  | U | U | H |
|  | T190 | 0.0 | 0.0 | B | B | R | B | B | C |
|  | T191 | 50.0 |  | H | U |  | U | U | H |
|  | T192 | 68.9 | 18.3 | H | H | ? | H | H | H |
|  | T194 | 66.7 |  | H |  |  |  |  |  |
|  | T197 | 5.6 |  | B | U |  | U | U | H |
|  | T198 | 72.2 |  | H | U |  | U | U | D |
|  | T200 | 61.1 |  | H | U |  | U | U | H |
|  | T201 | 44.4 |  | H | U |  | U | U | A |
|  | T203 | 66.7 |  | H | U |  | U | U | H |
|  | T205 | 50.0 |  | H | U |  | U | U | H |
|  | T206 | 0.0 | 0.0 | B | B | R | C | B | C |
|  | T207 | 0.0 |  | B | B | R | B | B | B |
|  | T209 | 55.6 |  | H | U |  | U | U | H |
| Rec | T211 | 44.4 |  | H | B |  | H | H | B |
| Rec | T212 | 2.5 | 8.9 | B | B | ? | B | B | B |
|  | T213 | ? |  | A | U |  | U | U | A |
|  | T214 | ? |  | A | U |  | U | U | H |
|  | T215 | 26.7 |  | H | U |  | U | U | H |
|  | T217 | 0.0 |  | B | B | R | C | B | B |
|  | T219 | 66.7 |  | H | U |  | U | U | H |
|  | T221 | 61.1 |  | H | U |  | U | U | H |
|  | T222 | 75.6 | 25.3 | A | U |  | U | U | A |
|  | T226 | 16.7 |  | B | U |  | U | U | B |
|  | T227 | 55.6 |  | H | U |  | U | U | H |
|  | T259 | 66.7 |  | H | U |  | U | U | H |
|  | T262 | 0.0 | 0.0 | B | B | R | B | B | B |
|  | T275 | 61.1 |  | H | U |  | U | U | H |
|  | T276 | 61.1 |  | H | U |  | U | U | H |
|  | T283 | 0.0 |  | B | B | R | B | B | B |
|  | T284 | 55.6 |  | A | U |  | U | U | H |
|  | T300 | 14.3 |  | B | U |  | U | U | H |

Legend:
A = homozygous P1 (=susceptible)
B = homozygous P2 (=resistant)
H = Heterozygous score
D = Between A and H
C = Between B and H
U = Unknown score
R = Individual resistant
S = Individual susceptible
Translated phenotype KG:
A = Overall % infected > 75
B = Overall % infected < 25
H = 25 < Overall % infected < 75
Note:
Rec are identified by De Ruiter Seeds

TABLE 6

Data generated by screening of two candidate linked markers to ToV resistance on 83 germplasm lines.

| Individual | P11/M35-F-216<N> CIS | Phenotype DRS | P13/M38-F-311<N> TRANS | P13/M38-F-313<N> CIS |
|---|---|---|---|---|
| T98_136_ | H | H | H | H |
| T578_1191_ | H | H | H | H |
| T579_1192_ | H | H | H | H |
| T793_1673_ | C | H | B | B |
| T71_80_ | H | H | H | H |
| T70_78_ | H | H | H | H |
| T78_89_ | H | H | H | H |
| T101_140_ | H | H | H | H |
| T102_141_ | H | H | H | H |
| T377_609_ | H | H | H | H |
| T286_461_ | H | H | H | H |
| T289_471_ | H | H | H | H |
| T06PF9 | B | A | A | A |
| T06OV6 | A | A | A | A |
| T06DE83 | A | A | A | A |
| T06DE84 | A | A | A | A |
| T06DE21 | A | A | B | B |
| T06DE142 | A | A | A | A |

TABLE 6-continued

Data generated by screening of two candidate linked markers to ToTV resistance on 83 germplasm lines.

| Individual | P11/M35-F-216<N> CIS | Phenotype DRS | P13/M38-F-311<N> TRANS | P13/M38-F-313<N> CIS |
|---|---|---|---|---|
| T06DE143 | A | A | A | A |
| T05GB1/05GB126BU | A | A | A | A |
| T05SP1 | B | A | A | A |
| T05SP2 | B | A | A | A |
| T05OT1 | A | A | A | A |
| T06MD44 | A | A | A | A |
| T06MD48 | A | A | A | A |
| T06MD50 | A | A | A | A |
| T06GL14 | A | A | A | A |
| T06GL15 | A | A | A | A |
| T06GL16 | A | A | A | A |
| T06GL17 | A | A | A | A |
| T06GL18 | A | A | A | A |
| T06GL19 | A | A | A | A |
| T06GL20 | A | A | A | A |
| T06GL21 | A | A | A | A |
| T06GL22 | A | A | A | A |
| T06GL23 | A | A | A | A |
| T06GL24 | A | A | A | A |
| T46_47_ | B | B | B | B |
| T43_44_ | B | B | B | B |
| T663_1367_ | B | B | B | B |
| T67_74_ | B | B | B | B |
| T06PF1 | B | B | B | B |
| T06PF8 | B | B | B | B |
| T06PF35 | B | B | B | B |
| T06HN28 | B | B | B | B |
| T06HN32 | B | B | B | B |
| T06HN91 | B | B | B | B |
| T06HN63 | B | B | B | B |
| T06HN67 | B | B | B | B |
| T06HN74 | B | B | B | B |
| T06HN98 | B | B | B | B |
| T06HT11 | B | B | B | B |
| T06HT13 | B | B | B | B |
| T06HT17 | B | B | B | B |
| T06HT18 | B | B | B | B |
| T06HT28 | B | B | B | B |
| T06HT3 | B | B | B | B |
| T06HT30A | B | B | B | B |
| T06HT31 | B | B | B | B |
| T06HT38 | B | B | B | B |
| T06HT7 | B | B | B | B |
| T06HT72A | B | B | B | B |
| T06HT8 | B | B | B | B |
| T06DS1 | B | B | B | B |
| T06TA109 | B | B | B | B |
| T06TA110 | B | B | B | B |
| T06TA122 | A | B | B | B |
| T06TA117 | B | B | B | B |
| T06TA130 | B | B | B | B |
| T06TA131 | B | B | B | B |
| T06TA120 | B | B | B | B |
| T06TA42 | B | B | B | B |
| T06TA0169 | B | B | B | B |
| T06TA85 | C | B | B | B |
| T06TA143 | B | B | A | A |
| T05OT2 | B | B | B | B |
| T05SP10 | C | B | B | B |
| T06GL69 | B | B | B | B |
| T06GL1 | B | B | B | B |
| T06GL93 | A | B | B | B |
| T06GL65 | B | B | B | B |
| T06GL50 | B | B | B | B |
| T06GL102 | B | B | B | B |

Legend:
A = homozygous P1 (=susceptible)
B = homozygous P2 (=resistant)
H = Heterozygous score
D = Between A and H
C = Between B and H
U = Unknown score

Example 2

Use of Marker C2_At5g25900 and Restriction Enzyme Mse I to Detect the Recessive Resistance for ToTV Sample:

A DNA sample of tomato tissue from each plant of a test population was prepared by using standard preparation techniques (microprep, e.g. as referred to in Fulton T M, Chunwongse J, and Tanksley S D. (1995) Microprep Protocol for Extraction of DNA from Tomato and other Herbaceous Plants. Plant Molecular Biology Reporter 13 (3): 207-209.).

The PCR Chemicals Were the Following:
dNTP's ($2_{13}$mM Stock) (Amersham Bioscience)
SuperTherm polymerase (Integro)
Forward primer (10_ng/μl) 5' TGC TAA TTG GGC TGA AAC TTA TGG (SEQ ID NO:7)
Reverse primer ($10_{13}$ ng/μl) 5' TGT TAG CTT TCT AGT TGA GAT GGA TG (SEQ ID NO:8)
10×_PCR buffer $25_{13}$ mM MgCl$_2$
Loading buffer
Ethidium_bromide (10mg/ml)
1× TE
0,5× TBE (Duchefa)
Restriction enzyme Mse I (New England Biolabs)

The PCR Mixture Consisted of (Per Sample):
2.0 μl 10× PCR buffer (25 mM MgCl$_2$)
2.0 μl dNTP's mix (2 mM of each dNTP's))
3.0 μl Forward primer (10 ng/μl)
3.0 μl Reverse primer (10 ng/μl)
0.05 μl SuperTherm polymerase
8.95 μl H$_2$O
1.1 μl template DNA The PCR Thermocycler Profile was as Follows:
3 min. @94° C.; (30 sec. @94° C., 1 min. @65° C., and 1 min. @72° C.) for 32 cycles; hold @4° C.

The PCR products were digested with Mse I following the manufacturer's instructions. Electrophoresis was performed in 1.5% agarose gels.

Markerscores:
Score 1=360 bp+260 bp=homozygous susceptible
Score 2=420 bp+360 bp+260 bp=heterozygous
Score 3=420 bp+260 bp=homozygous resistant
The phenotype was independently scored from hybrids.

Results and Discussion:

A photograph of the gel is presented in FIG. 2, showing the digested PCR products of the test population consisting of all three types of plants; migration is bottom to top, size markers indicate 100, 200, 300 bp etc. fragments).

TABLE I

| 2-Heterozygous | ToTV Markerscore | ToTV pheno |
|---|---|---|
| Plant 1002 | 2 | 2 |
| Plant 1003 | 2 | 2 |
| Plant 1004 | 2 | 2 |
| Plant 1006 | 2 | 2 |
| Plant 1007 | 2 | 2 |
| Plant 1010 | 2 | 2 |
| Plant 1011 | 2 | 2 |
| Plant 1012 | 2 | 2 |
| Plant 1014 | 2 | 2 |
| Plant 1015 | 2 | 2 |

TABLE II

| 3-Resistant | ToTV markerscore | ToTV Pheno |
|---|---|---|
| Plant 1016 | 3 | 3 |
| Plant 1017 | 3 | 3 |
| Plant 1018 | 3 | 3 |
| Plant 1019 | 3 | 3 |
| Plant 1037 | 3 | 3 |
| Plant 1038 | 3 | 3 |
| Plant 1040 | 3 | 3 |
| Plant 1041 | 3 | 3 |
| Plant 1042 | 3 | 3 |
| Plant 1043 | 3 | 3 |
| Plant 1044 | 3 | 3 |
| Plant 1045 | 3 | 3 |
| Plant 1046 | 3 | 3 |
| Plant 1047 | 3 | 3 |
| Plant 1048 | 3 | 3 |
| Plant 1049 | 3 | 3 |
| Plant 1051 | 3 | 3 |
| Plant 1052 | 3 | 3 |
| Plant 1054 | 3 | 3 |
| Plant 1055 | 3 | 3 |
| Plant 1061 | 3 | 3 |
| Plant 1062 | 3 | 3 |
| Plant 1064 | 3 | 3 |
| Plant 1065 | 3 | 3 |
| Plant 1066 | 3 | 3 |
| Plant 1067 | 3 | 3 |
| Plant 1068 | 3 | 3 |
| Plant 1069 | 3 | 3 |
| Plant 1070 | 3 | 3 |
| Plant 1071 | 3 | 3 |
| Plant 1072 | 3 | 3 |
| Plant 1073 | 3 | 3 |
| Plant 1074 | 3 | 3 |
| Plant 1075 | 3 | 3 |
| Plant 1076 | 3 | 3 |
| Plant 1077 | 3 | 3 |
| Plant 1078 | 3 | 3 |
| Plant 1079 | 3 | 3 |
| Plant 1080 | 3 | 3 |
| Plant 1081 | 3 | 3 |
| Plant 1082 | 3 | 3 |
| Plant 1083 | 3 | 3 |
| Plant 1084 | 3 | 3 |
| Plant 1089 | 3 | 3 |
| Plant 1090 | 3 | 3 |

TABLE III

| | ToTV markerscore | ToTV Pheno |
|---|---|---|
| 1-Susceptible | | |
| Plant 1020 | 1 | 1 |
| Plant 1021 | 1 | 1 |
| Plant 1022 | 1 | 1 |
| Plant 1024 | 1 | 1 |
| Plant 1025 | 1 | 1 |
| Plant 1026 | 1 | 1 |
| Plant 1027 | 1 | 1 |
| Plant 1028 | 1 | 1 |
| Plant 1029 | 1 | 1 |
| Plant 1030 | 1 | 1 |
| Plant 1031 | 1 | 1 |
| Plant 1032 | 1 | 1 |
| Plant 1033 | 1 | 1 |
| Plant 1034 | 1 | 1 |
| Plant 1035 | 1 | 1 |
| Plant 1036 | 1 | 1 |
| Plant 1056 | 1 | 1 |
| Plant 1057 | 1 | 1 |
| Plant 1058 | 1 | 1 |
| Plant 1059 | 1 | 1 |
| Plant 1085 | 1 | 1 |
| Plant 1086 | 1 | 1 |
| Plant 1087 | 1 | 1 |
| Plant 1088 | 1 | 1 |
| 1-Resistant | | |
| Plant 1039 | 1 | 3 |
| Plant 1050 | 1 | 3 |
| Plant 1053 | 1 | 3 |
| 3-Susceptible | | |
| Plant 1023 | 3 | 1 |
| Unknown | | |
| Plant 1005 | 3 | 2? |
| Plant 1008 | 3 | 2? |
| Plant 1013 | — | 2 |

The marker C2_At5g25900 was originally tested in 86 lines. Three of these lines could not be analysed because unclear phenotype or no marker results (see "unknown" in table III).

10 lines give score "2" while the phenotype was heterozygous susceptible.

24 lines give score "1" while the phenotype was homozygous susceptible.

45 lines give score "3" while the phenotype was homozygous resistant.

The markerscores coincide with the observed phenotype in 95% of the tested material.

Conclusions:

It was concluded that the marker can reliably (95% accuracy) be used for the prediction of the phenotype and for the detection of the resistance allele.

The genetic distance between the marker C2_At5g25900 and the resistance allele was mapped partially. Based on this marker, the data were inconclusive and the distance with the gene could only be determined reliably between a range of 0 and 10 cM.

When the same samples were tested for marker P13/M38-F-311/313, a total of 2 recombinants out of 55 samples could be accounted for, representing a linkage between this marker and the resistance gene of between 0 cM and 3.6 cM.

The invention claimed is:

1. A hybrid tomato plant of the species *Solanum lycopersicum* comprising commercially desirable characteristics, obtained by crossing a donor plant having within its genome a haplotype that confers resistance to tomato torrado virus (ToTV), as found in tomato breeding line T06PF1, a strain of said virus having been deposited with the Deutsche Sammlung von Mikroorganismen and Zellkulturen GmbH on 24 Nov. 2004 under depositor's reference number ToTV-E01 (DSM 16999), and a deposit of seed of said tomato line having been deposited with the American type Culture Collection (ATCC) on 6 Mar. 2014 under depositor's reference number 11 EFT 41822 (PTA-121067), wherein said haplotype is located in a genomic region of chromosome 4 between markers CT264 and TG163, linked to one or more markers selected from the group consisting of P14/M49-F-282, P11/M54-F-233/235, P11/M35-F-216, P21/M61-F-583, P25/M51-F-131, P015/M49-F-330, P13/M38-F-311/313 and C2_At5g25900, with a recipient plant comprising commercially desirable characteristics, wherein said obtained plant is produced by a method comprising screening for the presence of at least one molecular marker linked to said ToTV resistance haplotype, and wherein said haplotype is present in homozygous form.

2. The plant according to claim 1, wherein said resistance is expressed as a resistance to establishment of an infection.

3. A method of identifying the plant of claim 1, said method comprising performing a resistance bioassay using infection with said ToTV on offspring of a parental plant having within its genome a haplotype that confers resistance to tomato torrado virus (ToTV), as found in tomato breeding line T06PF1.

4. The plant according to claim 1, wherein the at least one molecular marker is selected from the group consisting of one or more of P14/M49-F-282, P11/M35-F-216, P21/M61-F-583, P25/M51-F-131, P15/M49-F-330, P13/M38-F-311/313 and C2_At5g25900.

5. A plant part of the plant of claim 1, comprising said haplotype.

6. The plant part according to claim 5, wherein said part is a fruit or a seed.

7. A tomato plant of the species *Solanum lycopersicum* obtained by crossing a donor plant having within its genome a haplotype as found in tomato breeding line T06PF1, a deposit of seed of said tomato line having been deposited with the American type Culture Collection (ATCC) on 6 Mar. 2014 under depositor's reference number 11 EFT 41822 (PTA-121067), in homozygous form that confers resistance to tomato torrado virus (ToTV) with a recipient plant comprising commercially desirable characteristics, wherein said haplotype is located in a genomic region of chromosome 4 between markers CT264 and TG163 linked to one or more markers selected from the group consisting of P14/M49-F-282, P11/M54-F-233/235, P11/M35-F-216, P21/M61-F-583, P25/M51-F-131, P15/M49-F-330, P13/M38-F-311/313 and C2_At5g25900, wherein said obtained plant is obtained by a) providing an inoculum of said ToTV;

b) exposing a tomato plant to said inoculum;

c) allowing for a sufficient incubation time; and d) selecting said tomato plant having within its genome the haplotype that confers resistance to ToTV if no infection establishes in said plant upon lapse of said incubation time.

8. A plant part of the plant of claim 1, comprising said haplotype.

9. The plant part according to claim 8, wherein said part is a fruit or a seed.

10. The plant according to claim 1, wherein the one or more markers are selected from the group consisting of P14/M49-F-282, P11/M35-F-216 and P13/M38-F-311/313.

11. The plant according to claim 1, wherein the one or more markers are selected from the group consisting of P11/M35-F-216, P13/M38-F-311/313 and C2_At5g25900.

12. The plant according to claim 1, wherein said haplotype is located in a genomic region positioned between AFLP markers P14/M49-F-282 and P11/M35-F-216 on chromosome 4.

13. The plant according to claim 1, wherein said haplotype is located in a genomic region positioned AFLP marker P13/M38-F-311/313 and COSII/CAPS marker C2 _At5g25900 on chromosome 4.

14. The plant according to claim 1, wherein said at least one molecular marker is selected from the group consisting of one or more of P14/M49-F-282, P11/M35-F-216, P13/M38-F-311/313 and C2_At5g25900.

15. The plant according to claim 1, wherein said at least one molecular marker is selected from the group consisting of one or more of P11/M35-F-216, P13/M38-F-311/313 and C2_At5g25900.

16. The plant of claim 1, wherein the haplotype is linked within 10 cM of markers P13/M38-F-311/313 and C2_At5g25900.

17. The plant of claim 1, wherein the haplotype is linked within 3.6 cM of markers P13/M38-F-311/313 and C2_At5g25900.

* * * * *

UNITED STATES PATENT AND TRADEMARK OFFICE
CERTIFICATE OF CORRECTION

| | | |
|---|---|---|
| PATENT NO. | : 8,946,506 B2 | |
| APPLICATION NO. | : 12/325310 | |
| DATED | : February 3, 2015 | |
| INVENTOR(S) | : Paulus Cornelis Maris et al. | |

It is certified that error appears in the above-identified patent and that said Letters Patent is hereby corrected as shown below:

In the Claims

Column 40, Line 57, Claim 1, please delete "P015/M49-F-330" and please insert

--P15/M49-F-330--

Signed and Sealed this
Thirtieth Day of June, 2015

Michelle K. Lee
*Director of the United States Patent and Trademark Office*

SEQUENCE LISTING

<160> NUMBER OF SEQ ID NOS: 8

<210> SEQ ID NO 1
<211> LENGTH: 409
<212> TYPE: DNA
<213> ORGANISM: Artificial Sequence
<220> FEATURE:
<223> OTHER INFORMATION: Amplification Primer

```
<400> SEQUENCE: 1
tctgggatca tatatgggat cttagaatgc tgaagtttcc agtccttgat ctccctggac      60
atactcactg gtaatactct gtggcaataa tgaagctgct tgccatctct ttaattagtt     120 gagttttga tataagatta ttgtctggtc cttcaatgtg tgtctcacta tgctgcctac     180
aacttaatga ctgctaactt ttttgttag ggtttagggt tagaagtttc tttctggatt     240
accatttcct tattgagtaa atgcagttga tgtttgttcg caggacatgg actgtcaagt     300
gcaatcccga acatgaagac ttaattctgg ttctttctct tcatttcctt tatctgtttg     360
tctaccctat gtatctggaa acatacttg tgcacactct cactgagcc                 409

<210> SEQ ID NO 2
<211> LENGTH: 491
<212> TYPE: DNA
<213> ORGANISM: Artificial Sequence
<220> FEATURE:
<223> OTHER INFORMATION: Amplification Primer

<400> SEQUENCE: 2
cttagaagct tccgcatgaa aatgaactgc aaacgtcata ctagataaaa ttaaagagac      60
ctcttgcaaa attctacatt ccacctcagc agcgttaact ccatcatgaa acatcaaga     120 atacagattt ggaggggat atactggagt gatacaaaca ttaataaaag agatgagtag     180
tgtggcaaag ggataatgag ctcaaaagat ggatcacgag ttcatactta cttcgagttg     240
tactgattta ttttcttgga agatgaggct tgattgattc tacaaccacc tgttaggaaa     300
aaaaatgcta aattaaaaca tgaaaacacg tggtgccaat tctcaactta aaataagaca     360
actctattag actattcatc atgtattaga ataatagca aattgccaag aatacatgca     420
cactcatggg aacattttct atgttatcct gaaattggct cagaagtcca acacaagaaa     480
agacacagat g                                                         491

<210> SEQ ID NO 3
<211> LENGTH: 278
<212> TYPE: DNA
<213> ORGANISM: Solanum Lycopersicum

<400> SEQUENCE: 3
agctcttgca agttgttcat cttctttcag ttgtgattca ctatctgcca aaaatcaaag      60
aaaaggaata attagaaaat caagcaaata tagttttggt caagcaaata aacaagtatg     120
gctggttctc aaaaattgtc aaagctaaac taataaaaag aagccagatt cctcatagaa     180
tgaaaagtat ttctatagaa caacgcgcaa taccatggat gagctaaata cacatacatg     240
aaagtactca gtagccttga acacatatga tgggaagt                            278

<210> SEQ ID NO 4
<211> LENGTH: 284
<212> TYPE: DNA
<213> ORGANISM: Solanum Lycopersicum

<400> SEQUENCE: 4
agctcttgca agttgttcat cttctttcag ttgtgattca ctatctgcca aaaatcaaag      60
gaaaggaata attagaaaat caagcaaata tagttttggt caagcaaata aacaagtatg     120
gctggttctc aaaaattgtc aaagctaaac taataaaaag aagctagatt cctcatagaa     180
tgaaaagtat ttctatagaa caacgcgcta taccatggat gagctaaact acacatacat     240
gaaagtactc agtagccttg aacacatatg atgggaagtt tact                     284
```

```
<210> SEQ ID NO 5
<211> LENGTH: 185
<212> TYPE: DNA
<213> ORGANISM: Solanum Lycopersicum

<400> SEQUENCE: 5
aatgagggaa cattcttttg ggcaaagtgg cattttctga taatcttctc acattcaaga      60
atggtatata actctttatg acttcacaaa tatcaactga tccattttgg actgcaaaat    120
ttgtgaactt cttttcctct gccataatta gtaaattata ttaccaaaca ataaaattgt    180
ttact                                                                 185

<210> SEQ ID NO 6
<211> LENGTH: 402
<212> TYPE: DNA
<213> ORGANISM: Solanum Lycopersicum

<400> SEQUENCE: 6
aaattgggct gaaacttatg gacctattta ttccatcaaa accggcgcaa atacaattgt      60
tgtactcagt tctagtgaac ttgcaaagga ggctatggtg actagatatt catccatctc    120
aactagaaag ctaacaaacg cattgagaat ccttacttgt gataagagta tagtcgcgat    180
aagtgattac gatgagtttc acaagacagc gaagcgccac atactgacca gtgttctagg    240
accaactgct cagaaacgct tccgtatcca cagggacacc ttggtagaaa atgtgtcaaa    300
gcaactacat gatttggtta ggactgatcc taacgaagca attaatctaa ggaagtcatt    360
tcagtcggaa cttttttggtt tagcattgaa acaagctttg gg                      402

<210> SEQ ID NO 7
<211> LENGTH: 24
<212> TYPE: DNA
<213> ORGANISM: Artificial Sequence
<220> FEATURE:
<223> OTHER INFORMATION: PCR Primer

<400> SEQUENCE: 7
tgctaattgg gctgaaactt atgg                                             24

<210> SEQ ID NO 8
<211> LENGTH: 26
<212> TYPE: DNA
<213> ORGANISM: Artificial Sequence
<220> FEATURE:
<223> OTHER INFORMATION: PCR Primer

<400> SEQUENCE: 8
tgttagcttt ctagttgaga tggatg                                           26
```